United States Patent
Olesen et al.

(10) Patent No.: US 8,780,181 B2
(45) Date of Patent: Jul. 15, 2014

(54) OPTICAL SECTIONING OF A SAMPLE AND DETECTION OF PARTICLES IN A SAMPLE

(75) Inventors: Tom Olesen, Gørløse (DK); Martin Christian Valvik, Hillerød (DK); Niels Agersnap Larsen, Lyngby (DK); Rasmus Helmsby Sandberg, Bagsværd (DK)

(73) Assignee: Unisensor A/S, Alleroed (DK)

( * ) Notice: Subject to any disclaimer, the term of this patent is extended or adjusted under 35 U.S.C. 154(b) by 344 days.

(21) Appl. No.: 13/132,713

(22) PCT Filed: Dec. 4, 2009

(86) PCT No.: PCT/DK2009/050321
§ 371 (c)(1),
(2), (4) Date: Jun. 3, 2011

(87) PCT Pub. No.: WO2010/063293
PCT Pub. Date: Jun. 10, 2010

(65) Prior Publication Data
US 2011/0261164 A1 Oct. 27, 2011

Related U.S. Application Data

(60) Provisional application No. 61/146,850, filed on Jan. 23, 2009.

(30) Foreign Application Priority Data

Dec. 5, 2008 (DK) .................................. 2008 01722

(51) Int. Cl.
*H04N 13/02* (2006.01)
*G01N 15/14* (2006.01)
*H04N 13/00* (2006.01)
*G01N 17/00* (2006.01)

(52) U.S. Cl.
CPC ....... *G01N 15/1475* (2013.01); *H04N 13/0239* (2013.01); *H04N 13/0055* (2013.01); *G01N 17/00* (2013.01); *H04N 13/0296* (2013.01)
USPC .................. 348/46; 348/45; 348/47; 348/48; 348/79; 348/80

(58) Field of Classification Search
CPC .............. G01N 15/1475; G01N 17/00; H04N 13/0239; H04N 13/0055; H04N 13/0296; H04N 13/049; H04N 13/0242
USPC .......................................................... 348/46
See application file for complete search history.

(56) References Cited

U.S. PATENT DOCUMENTS 3,814,522 A 6/1974 Clark et al.
3,921,622 A 11/1975 Cole
(Continued)

FOREIGN PATENT DOCUMENTS

JP 2007-322685 A 12/2007
RU 2232988 7/2004
(Continued)

OTHER PUBLICATIONS

International Search Report (Form PCT/ISA/210) mailed in International Application No. PCT/DK2009/050321 A1 Jan. 14, 2010, 3 sheets, Nordic Patent Institute, Taastrup, DK.
(Continued)

*Primary Examiner* — Andy Rao
*Assistant Examiner* — Shan Elahi
(74) *Attorney, Agent, or Firm* — Buchanan Ingersoll & Rooney PC

(57) ABSTRACT

The invention relates to an apparatus, a method and a system for obtaining a plurality of images of a sample arranged in relation to a sample device. The apparatus comprises at least a first optical detection assembly having an optical axis and at least one translation unit arranged to move the sample device and the first optical detection assembly relative to each other. The movement of the sample device and the first optical detection assembly relative to each other is along a scanning path, which defines an angle theta relative to the optical axis, wherein theta is larger than zero.

23 Claims, 11 Drawing Sheets

(56) References Cited

U.S. PATENT DOCUMENTS

| | | | |
|---|---|---|---|
| 4,448,534 A | 5/1984 | Wertz et al. | |
| 5,102,392 A | 4/1992 | Sakai et al. | |
| 5,123,275 A | 6/1992 | Daoud et al. | |
| 5,329,461 A | 7/1994 | Allen et al. | |
| 5,488,567 A | 1/1996 | Allen et al. | |
| 5,649,032 A | 7/1997 | Burt et al. | |
| 5,672,887 A | 9/1997 | Shaw et al. | |
| 5,672,888 A | 9/1997 | Nakamura | |
| 5,939,709 A * | 8/1999 | Ghislain et al. | 250/216 |
| 6,153,400 A | 11/2000 | Matsumura et al. | |
| 6,160,908 A | 12/2000 | Hakozaki | |
| 6,313,452 B1 | 11/2001 | Paragano et al. | |
| 6,656,683 B1 | 12/2003 | Reuben et al. | |
| 6,867,851 B2 * | 3/2005 | Blumenfeld et al. | 356/73 |
| 6,869,570 B2 | 3/2005 | Wardlaw | |
| 6,873,725 B2 | 3/2005 | Xu | |
| 6,919,960 B2 | 7/2005 | Hansen et al. | |
| 7,058,233 B2 | 6/2006 | Silber | |
| 7,068,365 B2 | 6/2006 | Hansen et al. | |
| 7,194,118 B1 | 3/2007 | Harris et al. | |
| 7,576,307 B2 | 8/2009 | Yazdanfar et al. | |
| 7,630,628 B2 | 12/2009 | Ogihara | |
| 7,634,128 B2 | 12/2009 | Snow et al. | |
| 7,634,129 B2 | 12/2009 | Strom | |
| 7,764,821 B2 | 7/2010 | Coumans et al. | |
| 7,860,302 B2 | 12/2010 | Sato et al. | |
| 7,949,161 B2 | 5/2011 | Kawanabe et al. | |
| 2002/0154216 A1 | 10/2002 | Yahiro | |
| 2003/0059866 A1 | 3/2003 | Lewis et al. | |
| 2003/0103277 A1 | 6/2003 | Mohwinkel | |
| 2003/0138139 A1* | 7/2003 | Strom | 382/154 |
| 2003/0151735 A1* | 8/2003 | Blumenfeld et al. | 356/73 |
| 2004/0008867 A1* | 1/2004 | Fein et al. | 382/100 |
| 2005/0068614 A1* | 3/2005 | Yoneyama et al. | 359/368 |
| 2005/0148085 A1 | 7/2005 | Larsen | |
| 2005/0179899 A1* | 8/2005 | Palti-Wasserman et al. | 356/417 |
| 2005/0259437 A1 | 11/2005 | Klein | |
| 2006/0084125 A1 | 4/2006 | Laor | |
| 2007/0009395 A1* | 1/2007 | Jiang | 422/104 |
| 2007/0122143 A1 | 5/2007 | Okamoto | |
| 2008/0011060 A1 | 1/2008 | Lynnworth | |
| 2008/0100703 A1* | 5/2008 | Yamada | 348/79 |
| 2008/0192128 A1 | 8/2008 | Kempe et al. | |
| 2008/0246946 A1 | 10/2008 | Hansen et al. | |
| 2009/0021260 A1* | 1/2009 | Stringer | 324/321 |
| 2009/0059362 A1 | 3/2009 | Jansen | |
| 2009/0231689 A1 | 9/2009 | Pittsyn et al. | |
| 2009/0239250 A1* | 9/2009 | Klug et al. | 435/29 |
| 2009/0295963 A1 | 12/2009 | Bamford et al. | |
| 2010/0208263 A1 | 8/2010 | Stevens et al. | |
| 2010/0314533 A1 | 12/2010 | Stallinga et al. | |
| 2013/0023041 A1* | 1/2013 | Greenberger et al. | 435/288.3 |

FOREIGN PATENT DOCUMENTS

| | | |
|---|---|---|
| WO | 89/01796 A1 | 3/1989 |
| WO | 98/56441 A1 | 12/1998 |
| WO | 02/055137 A2 | 7/2002 |
| WO | 02/084256 A1 | 10/2002 |
| WO | 2006/013312 A1 | 2/2006 |
| WO | 2007/036305 A1 | 4/2007 |
| WO | WO 2008/010761 A1 | 1/2008 |
| WO | WO 2008/134678 A1 | 11/2008 |

OTHER PUBLICATIONS

Written Opinion of the International Search Authority (Form PCT/ISA/237) mailed in International Application No. PCT/DK2009/050321 Jan. 14, 2010, 6 pages, Nordic Patent Institute, Taastrup, DK.

International Search Report dated Feb. 2011, issued in corresponding International Application No. PCT/DK2010/050327(3 pages).

International Search Report dated Jan. 14, 2010, issued in corresponding International Application No. PCT/DK2009/050321(3 pages).

Written Opinion of the International Search Authority (Form PCT/ISA/237) mailed in International Application No. PCT/DK2009/050321 mailed on Jan. 14, 2010 by the Nordic Patent Institute, Taastrup, DK (6 pages).

International Search Report, issued on Mar. 23, 2011, by the Denmark Patent Office in corresponding International Application No. PCT/DK2011/050064 (4 pages).

Decision on Grant issued in corresponding Russian Patent Application No. 2011127424/28(040583), dated Apr. 22, 2014, and translation thereof.

* cited by examiner

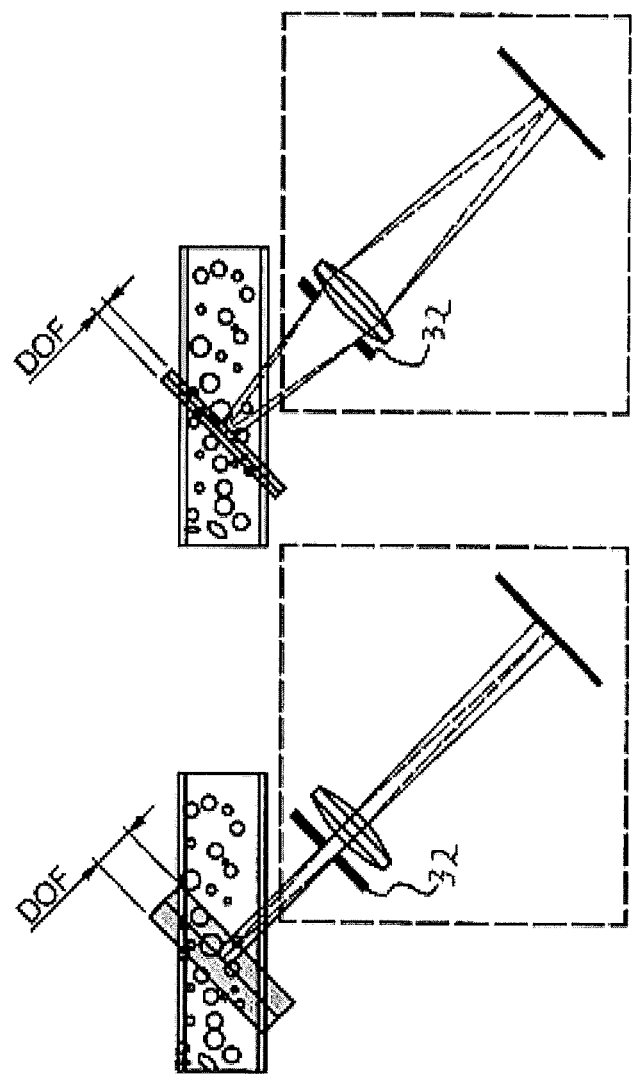

OPTICAL SECTIONING OF A SAMPLE AND DETECTION OF PARTICLES IN A SAMPLE

FIELD OF THE INVENTION

The invention relates to a method, an apparatus and a system for optical sectioning of a sample. The sample may be a confined inhomogeneous liquid sample comprising particles and the optical sectioning can be used for determining one or more parameters characterizing said particles. The invention also relates to determination of a volume of a confined sample so as to be able to determine the concentration of particles within the volume. The particles may be of biological such as embryo, bacteria, parasites, fungus, or cells. The cells may be blood cells, such as white and red blood cells, somatic cells, yeast cells, oozytes, blastocytes, cygotes, and thrombosites. The particles may also be of non-biological origin such as metal debris, water drops in oil, or air bubbles in liquids, pigments in paint, and pollution in water.

BACKGROUND OF THE INVENTION

The determination of the concentration of particles in a sample is often used, e.g. in connection with diagnosing a patient, where the concentration of white blood cells in a sample is one parameter used for determining the actual disease, or in connection with monitoring the state of a machine where the number of particles in a sample of oil from the engine may give an indication of any upcoming problems before they get critical.

Determination of the concentration of particles in a sample may be done by a number of methods. One of the methods is flow cytometry. Flow cytometry requires rather expensive equipment, firstly because the flow rate must be controlled and measured with very high accuracy to get a sufficiently precise measure of the volume, secondly because the detection system must work at short acquisition times in order to get reliable data from the particles present in the detector as they pass by. Laor (US 2006/0084125) describes a system for detection biological particles in a liquid sample where the liquid sample is flowing through a sample compartment and an object plane of an optical detection device has a non-zero angle to the flow direction.

Another method for determination of the concentration of particles in a sample is by microscopically viewing the sample either for manual or for automated detection and counting the particles confined in a certain well known volume. In patent application WO 2008/010761 by Olesen et al. such a method and apparatus is presented. In this method a portion of the sample is imaged onto an image recorder such as a 2-dimensional CCD-camera and the image is created by sending light through the sample towards the image recorder. The thickness of the imaged part of the sample is limited as the particles must be viewable and detectable through the sample. If the sample is too thick the light will be scattered and absorbed in the sample creating a poor quality image. Some of the particles in the sample may even be in the shadow of other particles making an accurate count difficult or impossible. The size of the image will be limited by the resolution of the image recorder and thereby the volume of the sample that may be used in the detection and counting of the particles will be limited. This is not a serious problem as long as the concentration of the particles to be counted is fitted to the size of the volume and the particle size. But if the concentration is high, an accurate measure may be difficult or impossible to determine. In this case a dilution of the sample could solve the measurement problem, but this knowledge may not be present until the measurement has been carried out. If the concentration is low the statistics for the measure will be poor, as small deviations in the count of particles or small deviations in the size of the volume may have great influence on the result. In this case the measurement should be carried out over a larger volume. Especially when using the method proposed by Olesen et al. in WO 2008/010761 for determining the distribution of different white blood cells the method may fall short. In this case it is important to have good statistics, but the sample volume is limited and if one or more of the white blood cell types have a low count, the statistical certainties may be poor.

In US 2008/0100703 Yamada describes a microscope system which makes a focus map of a sample with a large area compared to the area that can be imaged by the microscope. The information from the focus map is used when acquiring images of the different regions of the sample. These images are subsequently combined to provide a large scale image of the sample. The images of different sample regions are acquired by taking a plurality of images of one region at different depths and translating the sample and detection system relative to each other before images of another region is acquired. The translation of the sample and optical detection assembly relative to each other is parallel to the object plane of the optical detection assembly, i.e. the optical axis and the scanning path are perpendicular to each other, and the surface of the sample device is parallel to the object plane i.e. the normal of the surface is parallel to the optical axis.

SUMMARY

It is an object of the present invention to provide an apparatus, a method and a system for optical sectioning of a sample, where at least a part of the sample is scanned by translating the sample and an optical detection assembly relative to each other along a scanning path, and wherein the optical axis of the optical detection assembly has a non-zero angle relative to the scanning path.

In one embodiment, the apparatus, method and system according to the invention can be used for investigating an inhomogeneous liquid sample, where the analyzed volume is less limited by the optical detection assembly used to investigate the sample compared to the above discussed methods and which apparatus is simple to use. It has been found that the methods provided by using the apparatus and system of this embodiment simultaneously are beneficial compared to a method using flow cytometry and in particular it has been observed that at least a part of the problems and disadvantages of a flow assisted methods as experienced in flow cytometry may be avoided. The investigation of the inhomogeneous liquid sample may be useful for obtaining information about particles in the sample. The information can be the count of particles in the sample or it can be the concentration of the particles in a selected volume of the sample. The information can also be one or more parameters regarding the particles, such as size and type of the particles.

Thus, according to one embodiment of the present invention, there is provided an apparatus for obtaining a plurality of images of a sample arranged in relation to a sample device. The apparatus comprises at least a first optical detection assembly comprising at least a first image acquisition device. The first optical detection assembly has an optical axis and an object plane. The object plane comprises an image acquisition area from which electromagnetic waves can be detected as an image by the first image acquisition device. The apparatus further comprises at least one translation unit arranged to move the sample device and the first optical detection assembly relative to each other, and a housing arranged to support said first optical detection assembly and said translation unit, wherein said first optical detection assembly and said translation unit are arranged so that at least a part of said sample device is intersected by said image acquisition area. The movement of the sample device and the first optical detection assembly relative to each other is along a scanning path, which defines an angle theta relative to the optical axis, wherein theta is larger than zero.

The invention also comprises a method for obtaining a plurality of images of a sample. This method comprises arranging said sample in relation to a sample device and arranging said sample device in relation to an apparatus for obtaining a plurality of images. The apparatus comprises at least a first optical detection assembly having at least a first image acquisition device. The first optical detection assembly is having an optical axis and an object plane, where the object plane has an image acquisition area from which electromagnetic waves can be detected as an image by the first image acquisition device. The image acquisition area intersects at least a part of said sample. The sample device and said first detection assembly are moved relative to each other over a scanning length along a first scanning path. The scanning path and the optical axis together define an angle theta, which is larger than zero. The method furthermore comprises obtaining said plurality of images.

The invention also comprises a system for obtaining a plurality of images of a sample. The system comprises a sample device and an apparatus having at least a first optical detection assembly comprising at least a first image acquisition device. The first optical detection assembly of the apparatus has an optical axis and an object plane. This object plane comprises an image acquisition area from which electromagnetic waves can be detected as an image by the first image acquisition device. The apparatus of this system further comprises at least one translation unit arranged to move the sample device and the first optical detection assembly relative to each other, and a housing arranged to support said first optical detection assembly and said translation unit, wherein said first optical detection assembly and said translation unit are arranged so that at least a part of said sample device is intersected by said image acquisition area. The movement of the sample device and the first optical detection assembly relative to each other is along a scanning path, which defines an angle theta relative to the optical axis, wherein theta is larger than zero.

In principle, the scanning path may comprise any movement of the object plane and the sample relative to each other. In particular, the scanning path may comprise a substantially straight scanning line arranged along a scanning axis.

The scanning path may also be defined by a substantially rotational movement, in which case theta is the angle between said optical axis and the local tangential of said rotational movement. In one embodiment, the scanning path is confined to a plane, such as a straight line, a circular movement, a spiral movement, or any other suitable path.

In the context of the present application, the phrases "optics" and "optical" are used to describe the whole range of electromagnetic waves and in particular comprise electromagnetic waves with wavelengths from about 0.01 nm to about 15 km. In other words, the phrases "optics" and "optical" are not limited to electromagnetic waves in the visible range and devices for manipulating and detecting such waves, but may relate to the X-ray range, the ultraviolet range, the visible range, the infrared range, the ultra sound range and any other wavelength range that can be used for analyzing a sample.

Accordingly, the phrase "an image" is used to describe a spatially resolved recording of electromagnetic waves in the whole electromagnetic range including electromagnetic waves with wavelengths from about 0.01 nm to about 15 km. In other words, the phrase "an image" is not limited to images representing electromagnetic waves having wavelengths in the visible range, but also encompasses images presenting electromagnetic waves having wavelengths outside this range. An image can thus present signals in for example the X-ray range, the ultraviolet range, the visible range, the infrared range, the ultra sound range and any other wavelength range that can be used for analyzing and imaging a sample.

As used herein, an "optical detection assembly" is a unit comprising at least one image acquisition device capable of obtaining an image of electromagnetic waves that impinges on the acquisition device. The optical detection assembly optionally also comprises beam shaping and beam directing optics such as lenses, apertures, and mirrors.

The "optical axis" of the optical detection assembly is an imaginary line that defines a path along which light propagates from the sample to the image acquisition device. If the optical detection assembly comprises optical elements that can change the direction of the light path, the optical axis is defined as the imaginary line that defines a path along which light propagates from the sample to the first optical element that alters the direction of the light path.

The phrase "an inhomogeneous sample" is used to describe a sample comprising inhomogeneities that are not an inherent part of the basis material of the sample. A liquid sample containing biological particles or an oil sample containing debris are just two examples of an inhomogeneous sample.

In the context of the present application, the phrase "substantially at stand still" refers to a situation, wherein the movement of the particles in an inhomogeneous liquid sample does not affect the determination of the parameters of the sample, such as the parameters of particles in the sample. In one embodiment, substantially at stand still refers to the situation where the movement of the particles in the period of time lapsed in between the acquisition of two adjacent images in a sequence of spatially displaced images should be substantially smaller than the distance between these two adjacent images, such as one tenth of the distance. In one embodiment, substantially at stand still refers to the situation where there is no mass flow of said liquid sample during the acquisition of at least a part of said plurality of images. In one embodiment for imaging cells and their content, the movement of the cell may be limited to an extent whereby sufficiently sharp images of the cell can be obtained so that details relating to e.g. the nuclei can be determined. In embodiments adapted for determining parameters relating to cells, the term "substantially at stand still" thus may mean that the movement of said cells during the acquisition of an image may be limited to the Depth of Field (DOF) or a fraction of DOF, such as one thousandth of the (DOF), such as one hundredth of the DOF, such as one tenth of the DOF, such as one fifth of the DOF, such as one third of the DOF. The DOF may be in the range 0.1 micrometer to 200 micrometers. The movement of the particles in the liquid sample at stand still conditions may hence be less than 0.001 micrometer per second, such as less than 0.01 micrometer per second, such as less than 0.1 micrometer per second, such as less than 1 micrometer per second. The particle parameter may in this embodiment be the number and size of nuclei or the distance between the nuclei in a cell. In one embodiment where the details of the particle are of less interest, such as for counting particles, the limitation on the particle movement is such that the counting of the particles is not influenced by the movement. The movement of the particles to be counted may hence be less than 0.01 micrometer per second, such as less than 0.1 micrometer per second, such as less than 1 micrometer per second, such as less than 10 micrometer per second, such as less than 100 micrometer per second, such as less than 1 millimeter per second.

The depth of field is here defined as the range of distances from the imaging optics within which the image of the objects is substantially unaffected by displacements from the focal plane. The focal plane is defined as the plane where the best resolution of the imaging is attained. The term substantially unaffected implies that the estimated parameters, which characterizes the object features, are essentially unaffected by the translation. In one embodiment, substantially unaffected means that the ratio between the FWHM (Full Width Half Max) of the intensity distribution of a point source at a given position within the Depth of Field to the FWHM of the intensity distribution of a point source in the focal plane is less than 5, such as less than 2, such at less than 1.5, such as less than 1.25, such as less than 1.1, such as less than 1.05.

In one embodiment, the apparatus and the system according to the present invention comprises a storing device for storing the images acquired by the image acquisition device. The storing device may comprise a volatile type of memory unit, such as a random access memory unit or a non-volatile memory such as a hard disc, a flash drive, a CD-ROM, a DVD, a BlueRay disc or a similar storing medium.

The images recorded by the first image acquisition device may be analyzed using an image analyzing device. In one embodiment, the image analyzing device comprises pattern recognition algorithms. In one embodiment, these pattern recognition algorithms are adapted to compare a number of images depicting adjacent parts of a given sample, whereby it can determine when the particle is in the focal plane of the optical detection assembly. In one embodiment, the image analyzing device comprises an edge identifying unit for identifying edges of objects in the image(s). These edges may be identified as transitions between brighter and darker regions in said image.

In one embodiment, the position of a particle in a liquid sample is determined by analyzing a series of images obtained along said scanning path. The size of said particle in said images is evaluated in each image and a curve depicting the area of said particle in said images versus the position along said scanning path can be plotted. The minimum of this curve then represents the position of said object plane at which the particle is at focus, i.e. where the particle is localized in the focal plane.

In one embodiment, the system and apparatus according to the present invention is adapted to provide an optical sectioning of said sample. A combining unit may be arranged to combine the images of said optical sectioning to a 3D reconstruction of said sample. A 2D representation can also be realized by utilizing the invention. The image analyzing unit may be arranged to combine images from two or more scans along said scanning path and/or scans along different axes.

In one embodiment, the storage and/or analysis of the acquired images can take place at one or more external units and the apparatus and the system according to the present invention may comprise a connection unit for connecting to an external unit. The external unit may be a storage device and/or an image analyzing device as described above. The external device may in one embodiment comprise a personal computer, such as a laptop computer, equipped with a storage device and/or software to analyze said images. In one embodiment, the connection unit comprises a serial connection, such as an USB port. In one embodiment, the connection comprises a wireless connection, such as a General Packet Radio Service modem (GPRS), a Bluetooth antenna or a WiFi antenna. Also other forms of connection ports, such as an Ethernet connection or a parallel connection may be used. The connection unit may also comprise an internet connection for storing the images and other data on a remote storing device, such as a remotely placed server which collects images and data from one or more apparatuses. The data may be stored for later analyzing, or for reference use.

In one embodiment, the apparatus comprises at least one control unit arranged to control the translation unit and the acquisition of images by the first image acquisition device. The control unit may further comprise an analyzing device for analyzing the images acquired by the acquisition device.

In one embodiment, the apparatus and system according to the present application is adapted for determining at least one parameter of a volume of an inhomogeneous sample arranged in relation to said sample device. The parameter may in principle be any measurable parameter, such as the total number of particles in the volume, the number of specific particles in the volume, the number of different particles in the volume, the size of the volume or the shape of the volume.

For some applications, an analysis of a given sample requires that a predetermined number of particles are counted in order to provide a sufficiently low statistical uncertainty. One embodiment of said apparatus and said system is hence adapted to acquire and analyze images until a predetermined number of particles have been identified. The volume of the imaged and analyzed part of said sample may be determined simultaneously. The concentration of the particles in the sample may be determined using the determined volume of the imaged and analyzed part of the sample together with the predetermined number of particles. Also the number of particles in an inhomogeneous sample may be determined with a predetermined quality or certainty, and the concentration of the particles in the sample may be determined using the determined volume of the imaged and analyzed part of the sample. As it will be understood by the skilled person the quality of the analysis performed may accordingly be adjusted by the user, while simultaneously adjusting the analysis time, and thereby the quality versus time used may be optimized in a simple manner and within a large quality/time range.

During the measurement procedure a number of images are acquired each separated by a known step size. During acquisition it is therefore possible to calculate the effective volume of the measurement. The step size may be equal for all steps in a measurement, or they may be different.

In one embodiment the calculation of the effective volume is utilized to improve the statistics of the determination of the concentration of particles. During the measurement procedure the step sizes are accumulated and the acquired images are passed to a particle detection device adapted to detect particles. Detection of particles in an image is rather simple and may be done using dedicated software in dedicated hardware with the same speed as the image acquisition. When a particle in focus has been found, the total number of found particles is increased, and the measurement procedure continues until a certain number of particles have been found. The effective concentration may then be determined as concentration=number of particles/accumulated volume.

In one embodiment of the invention more information regarding a particle is needed. If e.g. the relative concentration of several different particles has to be determined, it may be necessary to do more calculations than may be done between two images acquired at normal speed. The image acquisition is stopped while the particle detection device determines the position of particles. After detection of a particle computing means for determining the actual type of the particle is activated. When the type of all particles in an image has been determined—or the particles have been discharged as being impossible to determine—the sample device is moved one step and the next image is acquired. It is not necessary to determine the volume of the sample measured as it is only the relative concentration that is interesting.

When a sufficiently high statistic certainty has been established for the relative concentration of the particles the measurement may be stopped. If e.g. the relative concentration of two different particles should be established, and the first particle has a high concentration and the second particle has a low concentration, the number of particles found of the second type should decide if sufficient particles have been found. If 1 out of 10 found particles is of the second type the statistic certainty is poor and the measurement should be continued. If 50 out of 500 particles are of the second type the statistic certainty is much better, and the measurement may be stopped. It may also be continued to establish an even better statistic.

In one embodiment of the invention information regarding presence of a particle characterised with specific parameters is needed. When e.g. a patient is suspected to be infected with malaria, a blood sample is taken and the blood is screened for malaria. This may require a large sample of blood to be screened compared to blood samples for determination of the concentration of white blood cells. After the blood sample is taken from the patient and inserted into the sample device the measurement is started. An image is acquired and the image analyzing device is activated to determine if a protozoa parasite such as Plasmodium falciparum and/or Plasmodium vivax is present. When the image has been inspected, the sample device is moved one step and the next image is acquired. For each step the accumulated volume is calculated. This procedure continues until either at least a certain number of malaria particles have been found or until at least a certain volume has been investigated.

In one embodiment, the image analyzing device comprises a boundary identifying unit arranged to identify at least one boundary of the sample in said images. The boundary unit may be arranged to identify at least one boundary of the sample in said images.

In one embodiment, the sample is arranged in a sample device comprising at least a first and a second confinement, which are substantially parallel to each other and the scanning path. The boundary identifying unit may then be arranged to identify a first boundary defined by the first confinement, and a second boundary defined by said second confinement. The boundary identifying unit may also be arranged to identify a third boundary defined by a third confinement, and a fourth boundary defined by a fourth confinement. The circumference of said sample in said sample device in a cross section perpendicular to said scanning path may be defined by said first to fourth boundaries. The third confinement may be substantially parallel to said scanning path and perpendicular to said first confinement, and the fourth confinement may be substantially parallel to said third confinement. In one embodiment, the second to fourth confinements comprise a flexible and at least partially transparent film arranged in contact with said sample.

The sample device may be arranged in relation to said optical detection assembly in such a way, that the normal vector of the first confinement and/or the second confinement is not parallel to the optical axis of the optical detection assembly. The angles $\text{psi}_{1\text{-}conf}$ and $\text{psi}_{2\text{-}conf}$ between the optical axis and the normal of the first and second confinements, respectively, hence is larger than zero.

In one embodiment, the sample is arranged on a sample device comprising a support, said support preferably being substantially parallel to said scanning path. The sample may be provided in any form, e.g. in the form of one or more drops of a liquid sample arranged on said support. A boundary identifying unit can then be arranged to identify the boundaries of the sample arranged on this support. A first boundary may then comprise an interface between said sample and said support, and a second boundary may comprise an interface between said sample and the surrounding atmosphere. In one embodiment, the sample device is arranged in a manner so that the support is located in between the sample image acquisition device and the sample.

The sample device may be arranged in relation to said optical detection assembly in such a way, that the normal vector of the support is not parallel to the optical axis of the optical detection assembly. The angle $\text{psi}_{support}$ between the optical axis and the normal of the support hence is larger than zero.

In one embodiment, wherein the boundaries of the sample and/or the boundaries of the image acquisition area are determined, the analyzed volume of said sample can be determined from a measurement of the separation of said boundaries. In one embodiment, the first and second boundaries are identified and the analyzed volume of said inhomogeneous sample is determined from the separation of these boundaries, together with the dimension of said image acquisition area, and the length of the scanned path. In one embodiment, the third and fourth boundaries of the sample are identified and the volume is determined from the separation of said first and second sample boundary, the separation of said third and fourth boundary, and the length of the scanned path. In one embodiment, cross sectional area of the sample volume in a cross section perpendicular to said scanning path is determined from the boundaries defined by said confinements and the volume is determined from the cross sectional area and the length of the scanned path.

In one embodiment, the analyzed part of said volume of said inhomogeneous sample is defined by the projection of said image acquisition area onto said cross sectional area and the length of the scanned path. This may be the situation when the image acquisition area does not comprise all the boundaries needed to define the cross sectional area of the confinements of said sample device.

In one embodiment, the sample is arranged in a sample device comprising a polygonal confinement. The boundary identifying unit may then be arranged to identify the boundary between the sample and the polygonal confinement. The longitudinal axis of said polygonal confinement may be substantially parallel to said scanning path. The determination of the size of the analyzed volume of said sample may comprise a measurement of the area of said polygonal confinement. The polygonal confinement may be a capillary tube.

In one embodiment, the sample is arranged in a sample device comprising a tubular confinement, such as a substantially cylindrical shaped confinement. The boundary identifying unit may then be arranged to identify the boundary between the sample and the tubular confinement. The longitudinal axis of said tubular confinement may be substantially parallel to said scanning path. The analyzed volume of said sample is determined from a measurement of the circumference of said tubular confinement. The tubular confinement may be a capillary tube.

In one embodiment, the apparatus and system according to the present invention comprises a unit for reading information provided by a coding on said sample device. The coding may comprise engraved or imprinted information relating to the position on the said sample device, allowing for a determination of where along said scanning path each of said plurality of images are acquired. In one embodiment, the position along said scanning path of an acquired image is obtained from using a reading from said at least a first translation unit. The knowledge of the specific position of one or more images may be very beneficial to the user and may e.g. be used for determining movements of particles within the sample. Other uses thereof will be clear to the skilled person e.g. from the following description.

The optical detection assembly according to the present invention comprises at least one optical element having a focal plane. The optical element may be any kind of lens or lens comprising system, such as an objective lens, e.g. a plano convex lens, a plano concave lens, a concave convex lens, a concave concave lens, a convex convex lens, a duplet, a triplet or a combination of 4 or more lenses. The focal plane of the optical element may coincide with the object plane of the optical detection assembly.

In one embodiment, the apparatus comprises a second optical detection assembly. The second optical detection assembly may be similar to the first optical detection assembly or different from the first optical detection assembly. The image acquisition area of said first optical detection assembly may intersect said image acquisition area of said second optical detection assembly at an intersection angle. The intersection angle may be in the range 0 to 180 degrees. In one embodiment, the intersection angle is zero and the image acquisition area of the first optical detection assembly coincides with the image acquisition area of the second optical detection assembly. In one embodiment, the intersection angle is 90° and the image acquisition area of the first optical detection assembly is perpendicular to the image acquisition area of the second optical detection assembly.

The first and second optical detection assemblies may be different, e.g. having different magnifications or viewing areas. The first and the second image acquisition areas may be different, e.g., different parts of the sample may be imaged by the two optical detections assemblies.

In one embodiment, said scanning path is substantially perpendicular to said object plane and the optical detection assembly may be arranged according to the Scheimpflug principle.

In one embodiment, the apparatus comprises a sample device base and the sample device may be arranged in relation to this sample device base when images of the sample are to be obtained. The sample device base may comprise a fixation unit for fixating said sample device to the sample device base.

The sample device base may comprise a substantially plane surface adapted to provide a base for said sample device, which may be arranged to in contact with said plane surface. In an embodiment, where said sample device comprises a first confinement and/or a second confinement, said sample device may be arranged with at least one of these confinements being substantially parallel to said plane surface. If the plane surface is arranged so that its normal has an angle $\psi_{base}$ relative to the optical axis of the optical detection assembly which is larger than zero, at least one of the angles $\psi_{1-conf}$ and $\psi_{2-conf}$ between the optical axis and the normal of the first and second confinements, respectively, are also larger than zero.

The angles between the optical axis and the normal vector of the first confinement, $\psi_{1-conf}$, second confinements $\psi_{2-conf}$ and said plane surface may be the range of from about 0.3 to about 89.7 degrees, such as in the range of from about 1 to about 89 degrees, such as in the range of about 2 to about 88 degrees, such as in the range of from about 4 to about 86 degrees, such as in the range of from about 5 to about 85 degrees, such as in the range of from about 8 to about 82 degrees, such as in the range of from about 10 to about 80 degrees, such as in the range of from about 20 to about 70 degrees, such as in the range of from about 25 to about 65 degrees, such as in the range of from about 30 to about 60 degrees, such as in the range of from about 35 to about 55 degrees, such as in the range of from about 40 to about 50 degrees. In one embodiment, $\psi_{1-conf}$ and $\psi_{2-conf}$ are in the range of from about 20 degrees to 89.5 degrees, such as in the range of from about 20 to about 85 degrees, such as in the range of from about 20 to about 80 degrees, such as in the range of from about 20 to about 75 degrees, such as in the range of from about 20 to about 65 degrees, such as in the range of from about 20 to about 55 degrees, such as in the range of from about 20 to about 45 degrees.

In one embodiment, the scanning and acquisition of images to obtain a plurality of images of the sample is performed so that the center of the images acquired along the scanning path are aligned substantially along a line with a monotonously changing line, such as a straight line or a line defining a circle, whereby an optical sectioning of the imaged sample volume can be realized.

If several optical sectionings of the sample are to be obtained, the translation stage may moves the optical acquisition device and the sample device relative to each other in between subsequent optical sectionings, i.e. the scanning and acquisition of images may be performed in several regions of the sample.

In one embodiment, the angle theta is relatively large, i.e. the object plane may be relatively close to being parallel to the scanning path, such that the area of said object plane than can intersect said sample in arranged in said sample device is relatively large.

The angle theta describing the angle between the scanning path and the optical axis of said optical detection assembly may be in the range of from about 0.3 to about 89.7 degrees, such as in the range of from about 1 to about 89 degrees, such as in the range of from about 2 to about 88 degrees, such as in the range of about 4 to from about 86 degrees, such as in the range of from about 5 to about 85 degrees, such as in the range of from about 8 to about 82 degrees, such as in the range of from about 10 to about 80 degrees, such as in the range of from about 20 to about 70 degrees, such as in the range of from about 25 to about 65 degrees, such as in the range of from about 30 to about 60 degrees, such as in the range of from about 35 to about 55 degrees, such as in the range of from about 40 to about 50 degrees. In one embodiment, theta is in the range of from about 20 degrees to 89.5 degrees, such as in the range of from about 20 to about 85 degrees, such as in the range of from about 20 to about 80 degrees, such as in the range of from about 20 to about 75 degrees, such as in the range of from about 20 to about 65 degrees, such as in the range of from about 20 to about 55 degrees, such as in the range of from about 20 to about 45 degrees, or such as in the range of from about 60 degrees to 89.5 degrees, such as in the range of from about 63 to about 86 degrees, such as in the range of from about 66 to about 83 degrees, such as in the range of from about 69 to about 80 degrees, such as in the range of from about 71 to about 78 degrees, such as in the range of from about 73 to about 77 degrees.

The size of image acquisition areas of identical optical detection assemblies is symmetric around theta equal to 90 degrees, and identical sizes of the image acquisition areas are obtained when theta equals $\alpha$ and $180-\alpha$ degrees, e.g., when theta equals 15 or 165 degrees.

In one embodiment, the optical detection assembly comprises beam shaping elements. This may e.g. be apertures inserted in the optical path to reduce image errors, beam enlarging and/or beam focusing elements, and/or image improving elements. The apertures may have a fixed size and have a fixed position in the optical path, or they may be an iris which may be changed according to requirements in the actual setup. If the measurement requirement is to have a large depth of field (DOF) the iris should be made small, while a requirement for a larger field of view with a smaller DOF, the iris should be made larger. An increase of the size of the iris will also reduce the requirement for light intensity to pass through the sample. In one embodiment, the aperture is positioned in between a beam focusing or beam enlarging element and said sample. The aperture may also be positioned in a releasable locked manner whereby it can be exchanged for example with an aperture having a different diameter of the opening.

A beam enlarging element may for example be a lens or two or more lenses in combination. The optical detection assembly may comprise image improving elements. This may by apertures or irises inserted in the optical path, or it may be special optical elements, such as prisms or wedges.

The image acquisition device may comprise a CCD chip or a CMOS chip, or a combination hereof if the apparatus comprises both a first and a second image acquisition device. The CCD and the CMOS chip may be used in a binned setup, where charge from adjacent pixels in a CCD is combined into one pixel during readout. This may be used for reducing the amount of data in measurement setups where the requirement for resolution is low when searching for particles in the sample. When a sample has been found, the binning may be changed or ended to get a higher resolution. In one embodiment, the apparatus and the system according to the present invention comprise a second image acquisition device with an image resolution that is higher than the resolution of said first image acquisition device.

The apparatus may further comprise a first translation unit for moving the sample device and the optical detection assembly relative to each other. This may be accomplished by moving the sample device relative to the housing of the apparatus while holding the optical detection assembly still, or vice versa moving the optical detection assembly relative to the housing of the apparatus while holding the sample device still.

The movement may be in a substantially continuous manner, and during the movement a plurality of images may be acquired with a predetermined time interval, said predetermined time interval being in the range of from about $10^{-9}$ s to about $10^3$ s, in the range of from about $10^{-4}$ s to about 10 s, or in the range of from about $10^{-3}$ s to about 1 s. Using this procedure, the images will be acquired with a predetermined spacing in the sample and the measurements will proceed fast, which in some cases is desirable, e.g. if the sample has a short lifetime. In one embodiment it is preferred that the image acquisition is performed fast so as to ensure that the sample appears to be at stand still.

The size of the step may be determined by information acquired from an image. If e.g. an interesting particle is found in an image, the next step could be to move the sample to get the particle in centre of the DOF to get the best possible image. On the other hand, if no particles have been detected in an acquired image, the step should be as long as possible to search the sample in as few steps as possible. There should always be an overlapping area between two steps to make sure that all particles present in the sample may be detected.

The size of the steps may in one embodiment be determined to a specific value which is kept constant during the measurement process. This may be used to acquire a set of images that may be combined into a 3-dimensional image or 3-dimensional measurement using the overlapping information in two subsequent images.

Sometimes 3D reconstruction of particles may require step sizes that are a fraction of the DOF.

In one embodiment, the Depth of Field (DOF) of said at least one optical element is larger than or equal to the step length of said translation unit.

The confinement in the X-direction sets an upper limit for the number of steps and thereby the number of different images that may be acquired. It is therefore preferred that the size of the sample in the X-direction is sufficiently large to comprise the desired number of steps in that direction.

The movement may in one embodiment be in substantially identical movement steps of a predetermined step length. Between two successive movement steps an image may be acquired. Using this procedure, the images may be acquired with a predetermined spacing in the sample. Furthermore the sample may be substantially at stand still when the image acquisition is performed. This may give better images with a better resolution than if the sample is moved during image acquisition The predetermined step length may be in the range from about 0.05 µm to about 1000 µm. Steps in size of up to about 1000 µm may be used in measurements where the sample is scanned for particles. The step length may even be larger than the DOF, as a particle may be detected even if it is outside the DOF area, as it will be imaged in a distorted manner. When a particle has been detected outside the DOF area, the step length may be changed to move the sample so as to get the particle within the image acquisition area.

The predetermined step length may for example be in the range from about 5 µm to about 10 µm. The optical detection system may for example be arranged to have a DOF within the range of from about 5 µm to about 10 µm, and in one embodiment of the invention it is preferred that the step size is smaller than the DOF to ensure that all particles are imaged in an undistorted manner.

The predetermined step length may therefore in one embodiment be smaller than the DOF, such as in the range from about 0.05 µm to about 5 µm. This is preferred for acquiring images used to get information for determining parameters for single particles such as the type of a white blood cell. The DOF of said at least one optical element may in one embodiment be larger than or equal to the step length of said translation unit thus allowing for a reliable stitching of the acquired images.

The predetermined step length may even be substantially smaller than the DOF, such as in the range from ⅕ DOF to ¹⁄₁₀₀ DOF. This is preferred for acquiring images used for 3D reconstruction of a particle in a sample.

The predetermined step length may be about 10 micrometers, about 5 micrometers, about 1 micrometer, or about 0.1 micrometer.

The apparatus may comprise a second translation unit for moving the sample device and the optical detection assembly relative to each other. The direction of the movement from the second translation unit may be substantially different from the direction of the movement of the first translation unit, and the direction of the movement from the second translation unit may be substantially perpendicular to the direction of the movement of the first translation unit.

A first translation unit may in one embodiment move the sample device and the at least a first optical detection assembly relative to each other in substantially rotationally manner. The rotational movement may in one embodiment be in substantially identical steps of a predetermined angular step. In between two successive steps an image may be acquired. The predetermined angular step may be in the range of from about 0.01 degrees to about 1 degree, in the range of from about 0.1 degree to about 0.5 degree. The predetermined step length may be 0.01 degrees, 0.02 degrees, 0.05 degrees, or 0.1 degrees.

A second translation unit may provide a radial translation of the object plane towards the center of rotation of the rotational movement provided by a first translation unit. The combined movements of said first and second translation stages may in principle resemble the motion of a light beam over a CD in a CD player.

In one embodiment, the apparatus and system according to the present invention comprises an image illumination device for exposing said sample to radiation. In principle this image illumination device can be any source of electromagnetic radiation, and the wavelength of said radiation may be in the range of from about 0.01 nm to about 15 km, in the range of from about 200 nm to about 1100 nm, in the range of from about 300 nm to about 800 nm, in the range of from about 400 nm to about 700 nm, in the range of from about 450 nm to about 600 nm, in the range of from about 495 nm to about 570 nm. The image illumination device may comprises a light source selected from the group of a laser, a diode laser, a LED, a light bulb, a supercontinuum source or a white light source.

In one embodiment, the electromagnetic radiation detected by said image acquisition device comprises light emitted as a result of a chemoluminescence process.

In one embodiment, the image analyzing unit is adapted to identify inhomogenities in an inhomogeneous sample. These inhomogenities may comprise particles, such as particles of biological or non-biological origin. The particles of biological origin may be embryo, bacteria, parasites, fungus, or cells. The cells may be blood cells, such as white and red blood cells, somatic cells, yeast cells, oozytes, blastocytes, cygotes, and thrombosites. The particles may also be of non-biological origin such as metal debris, water drops in oil, pigments in paint, and pollution in water.

In one embodiment, the apparatus and system according to the present invention is adapted for determining qualitative parameters of white blood cells in a sample and/or for determining the quantitative parameters of white blood cells in a sample In one embodiment, the number of red blood cells in a sample that are infected with protozoan parasites such as Plasmodium falciparum and Plasmodium vivax, is determined. This may be done in order to determine whether or not a patient is infected with e.g. malaria.

In one embodiment, the apparatus and system according to the present invention is adapted for evaluating the physical state of a cancer patient and said patient's readiness towards chemo-therapeutic treatment.

In one embodiment, the apparatus and system according to the present invention is adapted for detecting particles of non-biological origin, such as metal debris, water drops in oil, pigments in paint, and pollution in water.

The system and apparatus may comprise a housing. The housing may for example be fabricated in a partly or totally opaque material in order to keep all or merely some light e.g. with selected wavelengths from the surroundings away from said sample and said optical detection device.

In one embodiment, the apparatus and system according to the present invention comprises a feed back loop e.g. for repeatedly performing a sequence comprising: a) acquiring an image; b) analyzing said image; and c) adjusting the relative position of said sample device and said optical detection assembly. The feed-back loop may be adapted for tracing a particle in said sample.

In one embodiment, the apparatus and system according to the present invention further comprises further a sample preparing unit for sample preparation.

The system and the apparatus may be adapted to be a portable device further comprising a power source such as is a rechargeable battery.

In one embodiment the apparatus of the present is adapted to determine a value of at least one parameter describing microbial activity of individual biological organisms in a liquid sample. In such an embodiment, the image acquisition device is adapted to acquire images, wherein individual biological organisms may be identified, and the control unit is adapted to control the optical detection assembly and the translating unit to acquire images to form at least a first optical sectioning of biological organisms in said liquid sample. The liquid sample is arranged in a sample device comprising at least one sample container for holding a sample in liquid form. The image analysing device is arranged to analyse said first optical sectioning, said image analysing device comprises algorithms adapted to determine said value for said at least one parameter describing microbial activity of said individual biological organisms in each sample container. The control unit is adapted to sequentially acquire optical sectionings from said sample, such as said first optical sectioning and at least a second optical sectioning. The parameter describing microbial activity may in principle be any measurable parameter, such as, but not limited to, the cell division rate, cell viability living/dead rate, Brownian movements, metabolic rate, morphology, growth factor, kinetics or focus behaviour. The parameter may be understood to be a single value, a combination of several values or even a combination of several parameters. The phrase "biological organisms" may refer both to a single biological organism and an ensample of biological organisms, such as small or large groups of biological organisms. Microbial activity may be the understood to be the activity created by cell division, cell movements, metabolic induced changes to the environment, cell death etc. creating changes in the population of the microscopic organisms, changes in the size of single organisms or clusters of organisms, or changes in the position or movements of the organisms. Microbial activity may therefore be understood in a very broad context to every change detectable for a single microscopic organism or in small groups or in a population of microscopic organism. The number of sample containers in a sample device may vary depending on the application. A sample device which only comprises one sample container may for instance be used in an embodiment for monitoring one single biological organism. A sample device comprising several sample containers, such as 20 containers, may be used for susceptibility testing. The number of sample containers $N_{cont}$ on said sample device may be equal to 2, 3, 4, 5, 6, 8, 9, 10, 12, 14, 15, 16, 18, 20, 21, 22, 24, 25, 26, 27, 28, 30, or be more than 30. In one embodiment, the $N_{cont}$ sample containers are arranged in one or more rows, such as with the same number of sample containers in each row. The sample container may comprise an inlet to be used by the liquid to enter the sample container, and it may comprise an outlet to be used for ventilating excessive liquid or air during inlet of a liquid. The outlet may also be used for taking out the sample if the sample device is to be reused with a new sample of liquid sample.

The sample container may have an open confinement i.e. be open in at least one direction, in which case the container may be considered to be a well-type container, or the sample may have a substantially closed confinement i.e. be substantially closed in all directions, besides the optional inlet and outlet, in which case it may be considered to a cuvette-type container. The sample may be in liquid form while the optical sectioning is acquired.

The sample is considered to be in liquid form if the sample may flow by gravitational forces into the sample container or be drawn into the sample container using capillary forces. The liquid sample may behave as a gel. In the context of the present invention, a gel is a solid, jelly-like material that can have properties ranging from soft and weak to hard and tough. Gels exhibit substantially no flow when in the steady-state. By weight, gels are mostly liquid, yet they behave like solids Given an optical sectioning of a sample, the relevant biological organisms objects, be it cells, bacteria or other objects of interest, may be extracted for further analysis by applying a first algorithm comprising:

1. Applying a decision function on each pixel in the optical sectioning, classifying each pixel as either object or background. The decision function could for example be based on the local contrast around the pixel in question.
2. Combining the object pixels from each image of the optical sectioning to form individual object focus stacks. An object focus stack consists of one or more images of an object imaged in different focus planes. Care has to be taken when constructing the object focus stacks if the optical sectioning is acquired using an oblique optical system
3. For each object focus stack the point of optimal focus can be determined using a focus function, applied to each image in the object focus stack. In one embodiment, where the objects in question are amplitude objects, the variance of the pixel intensities may be used as a focus function. At the image of maximum variance the object is said to be in focus. This image may be extracted for further analysis.

In one embodiment of the invention the image analysing device comprise algorithms adapted to determine cell division rate. Given a set of optical sectionings of a sample at equidistant or non-equidistant time intervals the cell division rate is calculated by extracting the relevant cells using the first algorithm. For each object extracted a parameter regarding the cell may be calculated. This could for example be the number of sub components, the object area, the object perimeter, the size of the binary skeleton etc. The mean value of the parameter value for all objects in the optical sectioning may be calculated. This is repeated for all optical sectionings of the sample in question. By observing how the mean values vary over time, a cell division rate may be established. Other statistical measures than the mean of the parameter values may also be considered, such as the median, the variance, or other higher order and/or nonlinear statistical measures.

In one embodiment the image analysing device comprise algorithms adapted to determine cell viability. Given a single optical sectioning of a sample the degree of cell viability may be established by first applying the above mentioned method in order to extract the relevant object focus stacks. For each object the viability may be calculated by considering parameters such as the focus function behaviour, the intensity profile of the object in focus, the overall contrast of the object, the response of some biological staining etc. Applying this for all detected objects in the stack, statistical measures such as the mean can be used to judge the overall viability of the cells in the sample.

In one embodiment the image analysing device comprise algorithms adapted to determine living/dead rate. Given a set of optical sectionings of a sample at equidistant or non-equidistant time intervals the living/dead rate is calculated by extracting the relevant cells using the first algorithm. For each object extracted a parameter regarding living/dead properties may be calculated. This could for example be the focus function behaviour, the intensity profile of the object in focus, the overall contrast of the object, the response of some biological staining etc. The mean value of the parameter value for all objects in the optical sectioning may be calculated. This is repeated for all optical sectionings of the sample in question. By observing how the mean values vary over time, a living/dead rate may be established. Other statistical measures than the mean of the parameter values may also be considered, such as the median, the variance, or other higher order and/or nonlinear statistical measures.

In one embodiment the image analysing device comprise algorithms adapted to determine Brownian movements, which is determined by calculating. Given a single optical sectioning of a sample the degree of Brownian movements may be established by first applying the above mentioned method in order to extract the relevant object focus stacks. For each object focus stack the degree of movement may be calculated by considering the movement of the centroid of the object at different focus planes. Applying this for all detected objects in the stack, statistical measures can be used to judge whether the movement is Brownian, or if there for example is a desired flow direction of the objects in the sample.

In one embodiment the image analysing device comprise algorithms adapted to determine morphology parameters. Given a single optical sectioning of a sample the morphological parameters of the object in the sample may be established by first applying the above mentioned method in order to extract the relevant objects in focus. For each object in focus various morphological parameters may be determined e.g. the number of sub components, the form factor, the object perimeter, the circularity, the granularity, the circular variance etc. Applying this for all detected objects in the optical sectioning, statistical measures can be used to calculate the overall morphological parameters of the objects in the sample.

In one embodiment the image analysing device comprise algorithms adapted to determine morphology changes over time. Given a set of optical sectionings of a sample at equidistant or non-equidistant time intervals the cell division rate is calculated by extracting the relevant cells using said first algorithm. For each object extracted a parameter regarding the cell may be calculated. This could for example be the number of sub components, the form factor, the object perimeter, the circularity, the granularity, the circular variance etc. The mean value of the parameter value for all objects in the optical sectioning may be calculated. This is repeated for all optical sectionings of the sample in question. By observing how the mean values vary over time, the morphological changes over time may be established. Other statistical measures than the mean of the parameter values may also be considered, such as the median, the variance, or other higher order and/or nonlinear statistical measures.

In one embodiment, the growth factor of biological organisms is determined. The growth factor may be determined in order to e.g. extract information about how growth of the biological organisms is influenced by growth conditions, such as the sample environment and/or the introduction of one or more agents that interact with the biological organisms. In one embodiment the image analysing device comprise algorithms adapted to determine growth factor. Given a set of optical sectionings of a sample at equidistant or non-equidistant time intervals the cell division rate may be calculated by extracting the relevant cells using said first algorithm. For each object extracted a parameter regarding the cell may be calculated. This could for example be the number of sub components, the object area, the object perimeter, the size of the binary skeleton, the shape characteristics etc. The mean value of the parameter value for all objects in the optical sectioning may be calculated. This is repeated for all optical sectionings of the sample in question. By observing how the mean values vary over time, a growth curve may be established. Other statistical measures than the mean of the parameter values may also be considered, such as the median, the variance, or other higher order and/or nonlinear statistical measures.

In one embodiment the image analysing device comprise algorithms adapted to determine kinetics. Given a single optical sectioning of a sample the kinetics of the object in the sample may be established by first applying the above mentioned method in order to extract the relevant object focus stacks. For each object focus stack the degree of movement may be calculated tracking the movement of the centroid of the object at different focus planes. This may be done by applying simple 2D image correlation. Here after various kinetics parameters can be extracted, direction of movement, velocity etc. Applying this for all detected objects in the optical sectioning, statistical measures can be used to calculate the overall kinetic properties of the objects in the sample.

In one embodiment the image analysing device comprise algorithms adapted to determine focus behaviour. Given a single object image stack the focus behaviour can be analyzed by considering the focus function. Various measures may be determined, for example the modality of the focus curve can reveal optical properties such as if the object is an amplitude or phase object. Other measures such as the width of the focus curve may also be applied.

The method according to the present invention may be applied for determining microbial activity in a liquid sample by sequentially acquiring a plurality of optical sectionings of said liquid sample and selecting a first and a second optical sectioning from said plurality of sectionings. A value of at least one parameter for each optical sectioning is then computed and it is determined if a change in the value of the at least one parameter has occurred between the acquisition of the two optical sectionings. The method further comprises determining the microbial activity on the liquid sample from the changes in the value of the at least one parameter. The method according to the present invention may be applied for determining microbial activity in a liquid sample by acquiring at least one optical sectioning of said liquid sample and selecting a first optical sectioning from said at least one optical sectioning. A value of at least one parameter is computed for said first optical sectioning and determining said microbial activity in said liquid sample from said value of said at least one parameter.

In one embodiment of the invention, an external stimulation is applied to the liquid sample. A stimulating device may be arranged to provide stimulation to the liquid sample in a sample device such as to a liquid sample in a sample container. The stimulation may be e.g. be providing an electromagnetic field to the sample, providing a magnetic or electric field to the sample, or it may be applying an acoustic wave to the sample. Microscopic biological organisms may in one embodiment be imaged during stimulation to determine specific behaviour of the organisms which may help identify the species and nature of the organisms. The stimulating device may be controlled by the control unit to stimulate the sample container during image acquisition, or it may stimulate the sample container for a longer period to induce a more permanent change in the behaviour of the organisms.

In one embodiment of the present invention, the apparatus further comprises a liquid sample environment controlling device. The liquid sample environment controlling device may be adapted to control the physical environment of said biological organisms in said liquid sample, such as the temperature of said liquid sample. The liquid sample environment controlling device may also be adapted to control the chemical environment of said liquid sample, such as the pH value, the level of nutrition, the partial pressure of gasses such as oxygen, nitrogen and carbon dioxide, the salinity, the level of alkali metal ions such as $Li^+$, $Na^+$ and $Ka^+$, the level of alkaline earth metals, such as $Mg^{2+}$ and $Ca^{2+}$.

The microbial activity comprises the microbial susceptibility of said biological organisms towards an antibiotic agent.

In one embodiment of the present invention, at least one sample device is inoculated with at least a first agent, such as at least one sample container is inoculated with at least a first agent. Inoculation may be done before said liquid sample is introduced into said sample container or sample device, or it may be added after introducing the liquid sample to the sample container or sample device, i.e. while said liquid sample is in said sample container or sample device. The agent may be an antibiotic agent intended for destroying the biological organisms in the container, or it may be a nutrition agent intended for aiding the growth of the biological organisms. The agent may further be a cleaning detergent designed for destroying the biological organisms.

In one embodiment at least a part of the sample containers are inoculated with $N_{agent}$ different agents, where $N_{agent}$ may be 2, 3, 4, 5, 6, 8, 10, 20, or more than 20. It will be understood by a skilled person, that the number of different agents may depend on the measurement task at hand. If e.g. the susceptibility of bacteria to different kinds of bacteria is to be determined, it may be necessary to test using a large number of agents. In some cases the number of possible bacteria may be limited, and the number of different agents may be limited accordingly. In one embodiment, said sample containers are divided in groups of sample containers where the sample containers of each group are inoculated with the same agent and sample containers of different groups are inoculated with different agents, such as a first group of said sample containers being inoculated with said first agent, a second group of said sample containers being inoculated with a second agent, a third group of said sample containers being inoculated with a third agent, a fourth group of said sample containers being inoculated with a fourth agent.

A sample container or a sample device may also be prepared to probe e.g. the susceptibility of one biological organism toward several agents, such as a combination of agents. In one embodiment at least one sample container is inoculated with several different agents.

In one embodiment, at least one sample container is substantially free of an agent. By substantially is meant that the amount of agent present in the container should be smaller than the amount of agent necessary to create an influence on the organisms it the container.

In one embodiment a first agent is inoculated in different concentrations in at least two different sample containers. When determining Minimum Inhibitory Concentration (MIT) which indicates the concentration of the antibiotic necessary to prevent the micro organisms to grow it is advantageous to use several different concentrations is different containers at the same time. This speeds up the measurements, and the measurements may be compared as they may have been acquired using the same conditions and environment. In some cases it may be preferred that at least 5 or 10 different concentrations of agents are used when determining MIT. I other cases a different number of different concentrations of agents is preferred, such as below 5 concentrations or above 10 concentrations.

In one embodiment the control unit is adapted to acquire optical sectionings from at least one sample device or container over a period of time. The optical sectioning comprises at least one image, and in many cases several images. For some applications and biological organisms, the period of time used to acquire the optical sectioning(s) may be relatively long such as several days or several hours. For other applications and biological organisms the period for acquiring optical sectionings may be considerable shorter. In one embodiment, said period of time is below about 144 hours, such as below about 72 hours, such as below about 48 hours, such as below about 36 hours, such as below about 24 hours, such as below about 18 hours, such as below about 12 hours, such as below about 8 hours, such as below about 5 hours, such as below about 4 hours, such as below about 3 hours, such as below about 2 hours, such as below about 1.5 hours, such as below about 1 hours, such as below about 2700 seconds, such as below about 1800 seconds, such as below about 900 seconds, such as below about 600 seconds, such as below about 480 seconds, such as below about 300 seconds, such as below about 120 seconds, about 60 seconds, such as below about 10 seconds, such as below about 5 seconds, such as below about 2 seconds, such as below about 1 second. It will be appreciated by a skilled person that the mentioned periods are given in way of example and that the period may be varied depending on the measurement to be performed, and the period may be changed during measurement depending on the value of the parameter determined during measurement, such as changed individually for the different sample containers.

The apparatus and method according to the present invention may be used to determine the microbial activity of biological organisms located in a plurality of sample containers. The control unit may be adapted to sequentially acquire optical sectionings from at least two different sample containers. In one embodiment optical sectionings are acquired from at least two different sample containers with a first time interval between the acquisition of following two optical sectionings. The first interval may be below about 1800 seconds, such as below 900 seconds, such as below 600 seconds, such as below 300 seconds, such as below 120 seconds, such as below 60 seconds, such as below 30 seconds, such as below 10 seconds, such as below 5 seconds such as below 2 seconds such as below 1 seconds such as below 0.5 seconds such as below 0.2 seconds such as below 0.1 seconds, such as below 0.01 seconds such as below 0.001 seconds.

The apparatus and method according to the present invention may determine the microbial activity of one or more biological organisms located in sample containers from a plurality of optical sectionings. The control unit may be adapted to sequentially acquire the optical sectionings. In one embodiment, said optical sectionings are sequentially acquired from a sample container with a second interval in time between two subsequent optical sectionings from the sample container. The interval may vary depending on the measurement to be performed. The second time interval may be below about 3600 seconds, such as below 1800 seconds, such as below 900 seconds, such as below 600 seconds, such as below 300 seconds, such as below 120 seconds, such as below 60 seconds, such as below 30 seconds, such as below 10 seconds, such as below 5 seconds such as below 2 seconds such as below 1 seconds such as below 0.5 seconds such as below 0.2 seconds such as below 0.1 seconds, such as below 0.01 seconds such as below 0.001 seconds. If the microbial activity of the sample is high, it may be advantageous to use a short interval, while a low microbial activity may call for a longer interval without losing important information. The interval may be changed during measurement depending on the determined value of the parameter, such as changed individually for the different sample containers.

In one embodiment, the control unit is adapted to stop image acquisition when the value of the parameter satisfies a predetermined condition. The predetermined condition may be related to the determination of antibiotic susceptibility of said biological organisms or it may be related to the determination of the minimum inhibitory concentration (MIT).

BRIEF DESCRIPTION OF DRAWINGS

Embodiments of the invention will now be described in further detail by way of example under reference to the accompanying drawings where FIG. 11 shows schematics of the correlation of the Depth of Field and the size of an iris inserted on the optical axis.

The figures are schematic and may be simplified for clarity. Throughout, the same reference numerals are used for identical or corresponding parts.

DETAILED DESCRIPTION OF THE PREFERRED EMBODIMENTS

Figure 1:
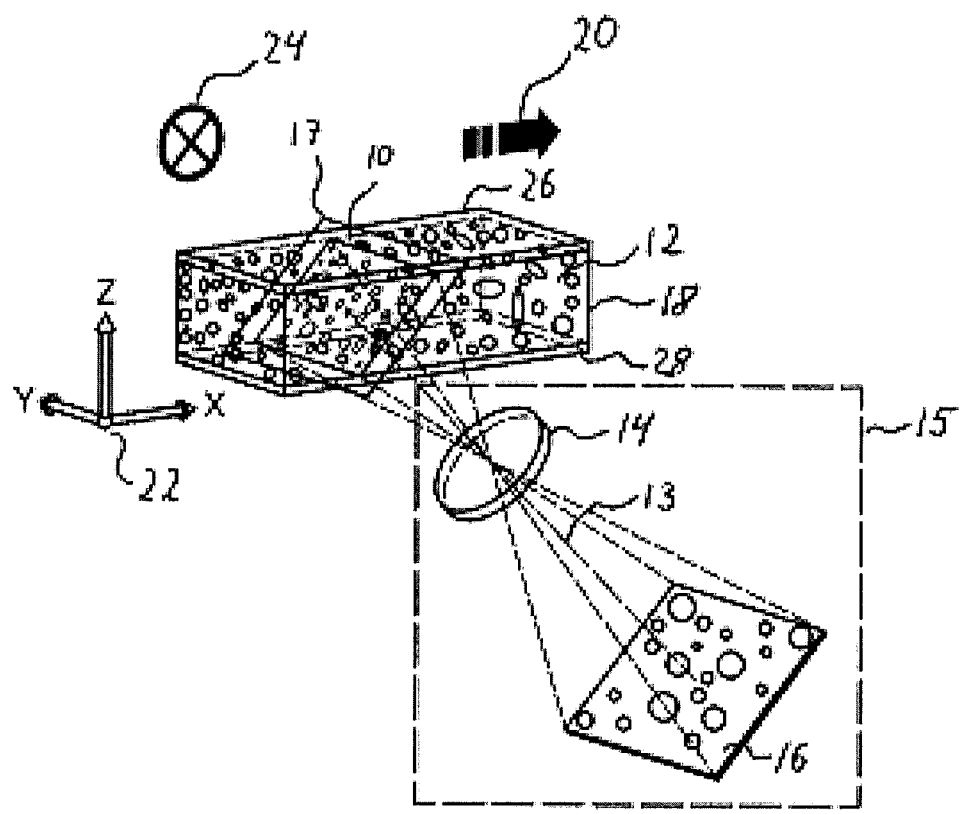
FIG. 1 shows a schematic perspective view of a measurement apparatus according to one embodiment of the present invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The invention is defined by the features of the independent claim(s). Preferred embodiments are defined in the dependent claims. Any reference numerals in the claims are intended to be non-limiting for their scope.

Some embodiments have been shown in the foregoing, but it should be stressed that the invention is not limited to these, but may be embodied in other ways within the subject-matter defined in the following claims.

Referring to FIG. 1 one embodiment of the present invention will be described. A sample device 18 comprising a sample 12 is shown. Referring to the coordinate system 22 the sample device 18 has a first confinement 26 and a second confinement 28 confining the sample 12 in the Z-direction. The sample device 18 may extend beyond an image acquisition area 10 in the X-direction as well as in the Y-direction. Especially in the X-direction it is preferred that the sample device 18 extends beyond the initial image acquisition area 10. It is however preferred that the sample 12 is confined in all three dimensions to make sure the sample 12 is at a non-moving state or steady state when performing the measurements.

An image illuminating device 24 illuminates the sample 12 within the sample device 18. The first confinement 26 and the second confinement 28 are made of a material transparent for the electromagnetic waves from the illuminating device 24.

An optical detection assembly 15 comprises an image acquisition device 16 and an objective lens 14. The objective lens 14 comprises a first optical axis 13 and an object plane 17 perpendicular to the first optical axis 13. The image acquisition area 10 of the sample 12 is arranged to be coinciding with the object plane 17 of the objective lens 14. This enables a 2-dimensional image or 2-dimensional measurement of the image acquisition area 10 of the sample 12 to be imaged onto the image acquisition device 16.

It is preferred that the image acquisition area 10 intersects the first confinement 26 as well as the second confinement 28, in order to get the first confinement 26 and the second confinement 28 imaged onto the image acquisition device 16 and thereby comprised in the images.

The sample device 18 may be moved relative to the optical detection assembly 15 using a translation stage 20—in the figure symbolized by an arrow. The sample device 18 may be moved in the X direction in steps and for each step an image from the image acquisition device 16 is captured and stored in an image storing device for later use. The movement in the X direction intersects the first optical axis 13.

Figure 6:
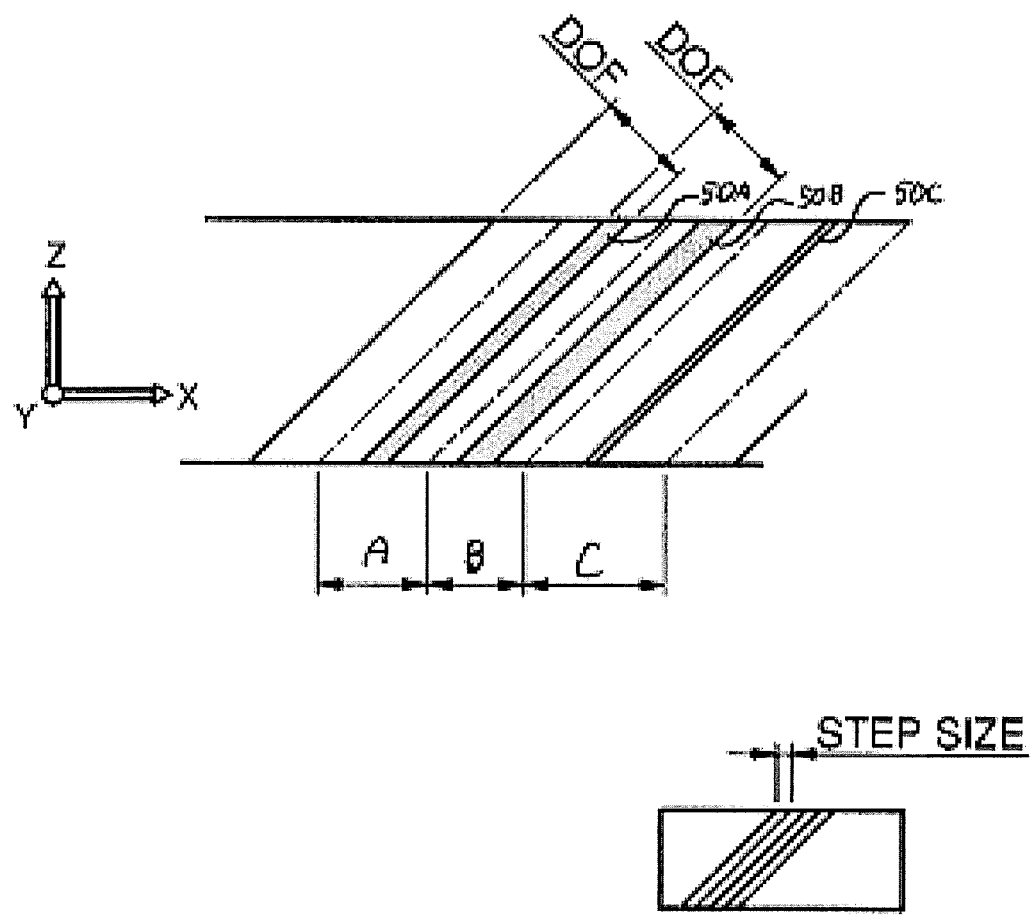
FIG. 6 shows a schematic view of the correlation between the Depth of Field and the step size of the translation of the sample device.

The step size of the movement in the X direction is defined by using the Depth of Field (DOF) of the objective lens 14—see FIG. 6. The Depth of Field is the portion of a scene that appears sharp in the image. It is preferred that the step size is smaller than the DOF. This ensures that two subsequent images captured by the image acquisition device 16 have an overlapping part 50. The overlapping part 50 may be different from step to step. In FIG. 6 an image No. 1 is acquired from the first position of the sample device. Then step A is made, and an image No. 2 is acquired. The size of the overlapping area is the greyed area 50A. Then a smaller step B is made, and image No. 3 is acquired. The size of the overlapping area is the greyed area 50B. The area 50A is smaller than the area 50B as the step B is smaller than the step A. A new step C is then made, and an image No. 4 is acquired. The step C is larger than the previous two steps, and the overlapping area 50C is smaller than previous.

In one embodiment of the invention a translation stage for moving the sample device 18 in the Y-direction is used to enlarge the measurement volume. It is therefore preferred that the size of the sample in the Y-direction is sufficiently large to comprise the desired number of steps in that direction.

The image acquisition area 10 may extend beyond the sample device 18, or at least extend beyond the first confinement 26 and the second confinement 28 of the sample device 18. The acquired images may comprise an image of the two confinements, and this information may be used to determine the height of the image acquisition area 10 and subsequently the distance between the two confinements.

A calibration of the apparatus of the invention may establish the width of the image acquisition area 10 in the Y direction and combining the width and the height of the image acquisition area 10 gives the "true" image acquisition area.

Figure 3:
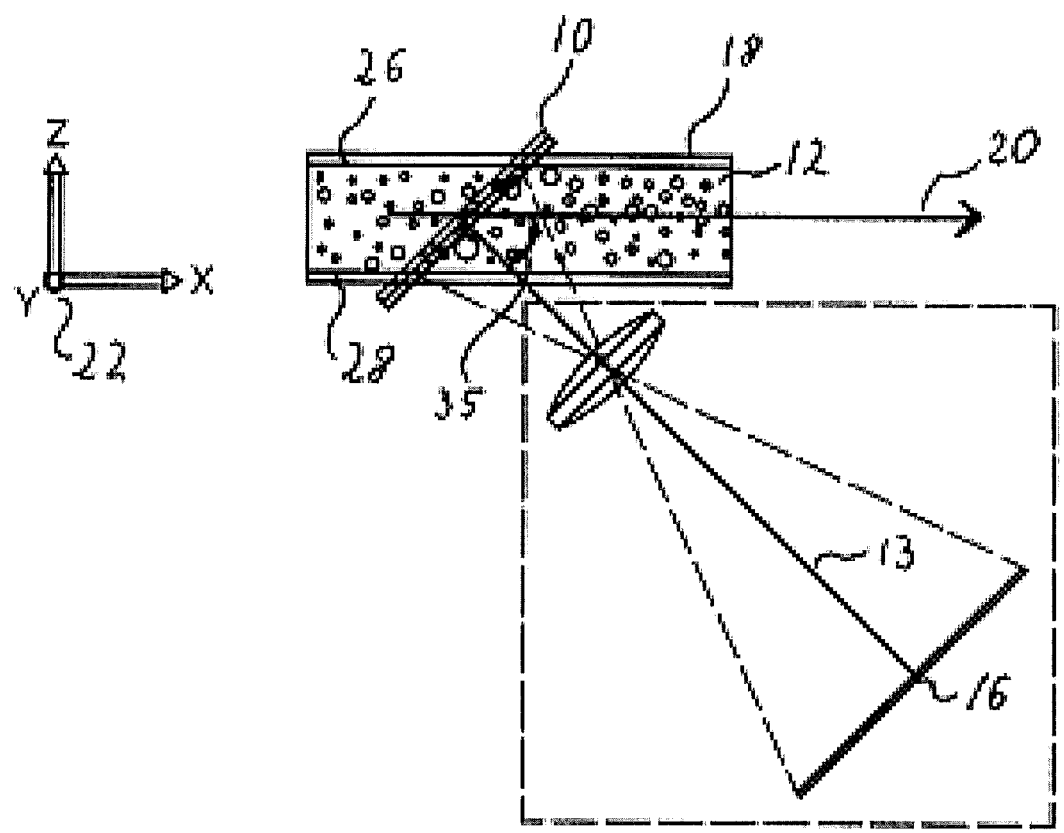
FIG. 3 shows a schematic side view of a measurement apparatus according to one embodiment of the invention.

Referring to FIG. 3 a preferred embodiment of a sample device 18 will be described in detail. The sample device 18 comprising a sample 12 is shown. Referring to the coordinate system 22 the sample device 18 has a first confinement 26 and a second confinement 28 confining the sample 12 in the Z-direction. The sample device 18 may extend beyond the image acquisition area 10 in the X-direction as well as in the Y-direction, or the sample device 18 may be smaller than the image acquisition area 10.

The angle theta 35 is defined as the angle between the first optical axis 13 and the scanning axis X as defined by the coordinate system 22. In one embodiment, the angle theta is in the range 5 to 85 degrees.

It is in one embodiment preferred that the image acquisition area 10 intersects the first confinement 26 as well as the second confinement 28 in order to get the first confinement 26 and the second confinement imaged onto the image acquisition device 16 and thereby comprised in the images. Especially in the X-direction it is preferred that the sample device 18 extends beyond the initial image acquisition area 10. It is in one embodiment however preferred that the sample 12 is confined in all three dimensions to make sure the sample 12 is at a non-moving state or steady state when performing the measurements.

The confinement in the X-direction sets an upper limit for the number of steps and thereby the number of different images that may be acquired. It is therefore preferred that the size of the sample in the X-direction is sufficiently large to comprise the desired number of steps in that direction.

In one embodiment of the invention a translation stage for moving the sample device 18 in the Y-direction is used to enlarge the measurement volume. It is therefore in one embodiment preferred that the size of the sample in the Y-direction is sufficiently large to comprise the desired number of steps in that direction.

It is preferred that the first confinement 26 and the second confinement 28 are made of a material transparent to the electromagnetic waves transmitted from an illuminating device and from the electromagnetic waves that may be transmitted from the sample 12. The material may be a transparent plastic or it may be glass. It is often preferred that the first confinement 26 and the second confinement 28 are parallel to each other.

Figure 2:
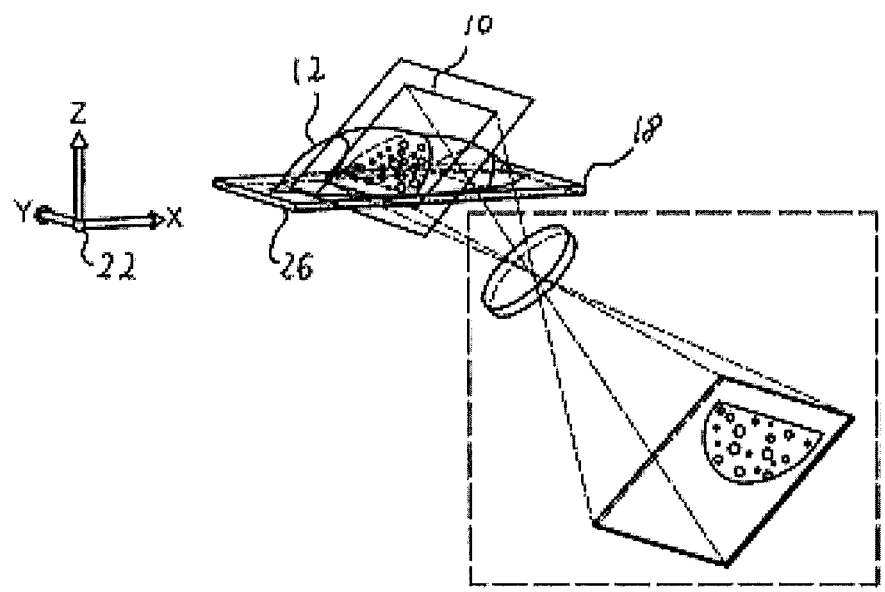
FIG. 2 shows a schematic perspective view of a sample in a sample device with one support.

The first confinement 26 may be a transparent foil, covering the sample thereby not being parallel to the other plate. If the sample is of low viscosity or even solid matter measurements may be carried out without a first confinement—see FIG. 2. In FIG. 2 a sample device 26 comprising a sample 12 is shown. The sample may be a drop of blood or other fluid but it is often preferred that the viscosity is low. In this case, the first confinement is comprised in the surface of the sample.

The sample device may comprise a channel with a rectangular cross section. The dimensions of the channel may for example be H×W×L=100 μm×2 mm×5 cm. It is in one embodiment preferred that the sample device may be moved along the entire length of the channel.

The sample device may in one embodiment be confined within a rotating disc, and a stationary camera may record a ring-shaped partial volume of the disc, such as tracks on a CD. Additionally, the camera may move in the radial direction in order to record the entire volume of the disc. In one embodiment, the scanning of the sample device is similar to the principle of playing a CD, where the laser head moves from the centre and out.

The translation of the sample device relative to the camera may be achieved in a number of ways, e.g. by using a translation stage in one or two dimensions (X, Y translation). The translation may also be a rotation of a disc and translation towards the center (R, θ).

The translation may be made in accurate steps determined either by a calibration of the "motor" prior to the measurement, or determined by using a code comprised in the y-confinement of the sample device.

The images acquired by the image acquisition device may be stored on a storing device. The storing device may be any kind of storing device capable of storing images. The storing device may for example comprise a volatile memory unit that requires power to maintain the stored information. One example of a volatile type of memory units is a random access memory unit such as a dynamic random access memory and static random access memory. The storage device may also comprise a non-volatile memory that can retain the stored information even when not powered. Examples of non-volatile memory include hard disc, flash, CD-ROM, DVD, Blu-eRay, read-only memory, flash memory, or similar storing medium.

The image illuminating device 24 shown in FIG. 1 is preferable arranged to transmit electromagnetic waves through the image acquisition area 10 in the sample device 18 towards the image acquisition device comprised in the optical detection assembly 15. The image illuminating device 24 may also be arranged in other positions relative to the sample depending on the actual form of the apparatus and the requirements for the illumination of the sample.

It is often preferred that the first confinement 26 and the second confinement 28 are made of a material transparent for the electromagnetic waves from the illuminating device 24.

The illuminating device 24 is in one embodiment arranged to transmit electromagnetic waves with a wavelength of about 495 nm to about 570 nm also known as green light, but the light may also have other wavelengths in the range of about 0.01 nm to about 15 km. The light may come from a laser, such as a diode laser, from a LED, a light bulb or from other standard light sources.

Other illuminating techniques may also be used, such as polarisation, photoluminisence, phosphorescence and electroluminescence.

The illuminating device 24 may comprise more than one single light source. In one embodiment the illuminating device comprises both a visible red LED and an infrared LED. The illuminating devices may be switched on separately for illuminating the sample for two different views. E.g. one illuminating device may be used for counting the number of a specific cell type in the sample, while the other illuminating device may be used for determining a parameter describing the specific cell type.

The optical detection assembly 15 comprises at least one image acquisition device 16. The image acquisition device 16 may be any kind of digital camera, such as a CCD- or CMOS camera.

The optical detection assembly 15 may comprise one or more lenses for shaping the beam and for enlargement of the images. The optical detection assembly 15 may also comprise other optical elements such as mirrors, irises, wedges, prisms, holograms, Fresnel-lenses, etc.

Figure 7:
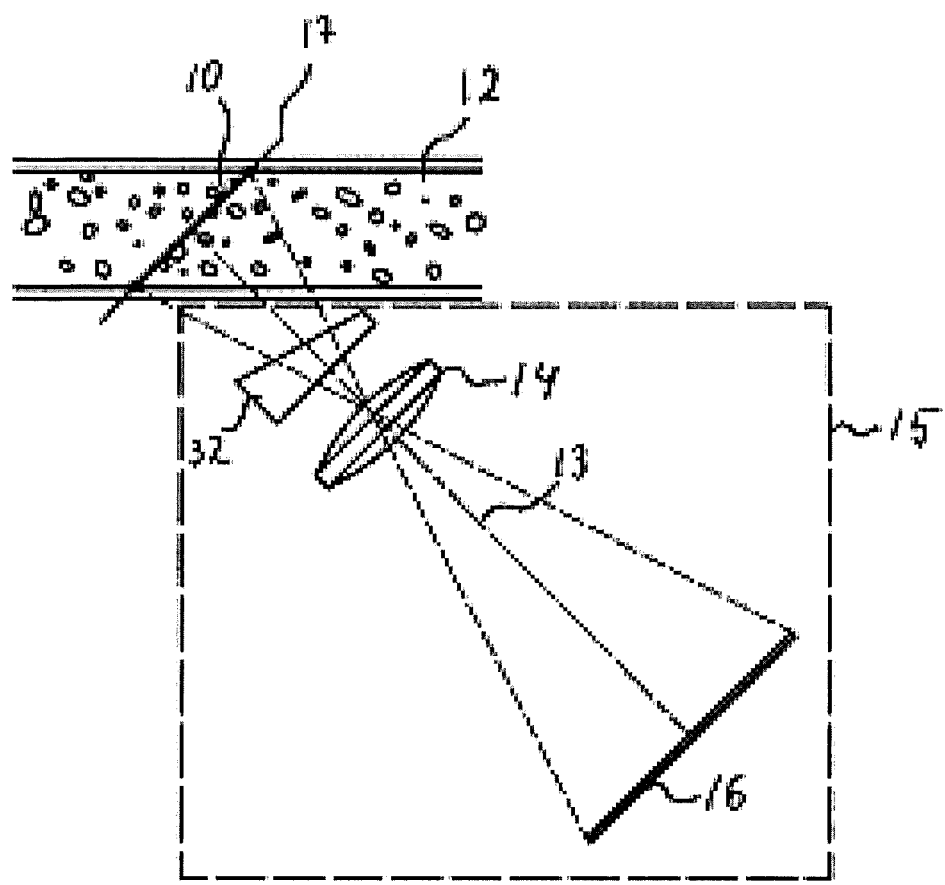
FIG. 7 shows a schematic side view of an image improving element that may be used in connection with one embodiment of the present invention.

In FIG. 7 an image improving element 32 is shown. The slanted imaging of the sample may introduce image errors making detection of particles more difficult. An image improving element 32 may be inserted in the optical path between the sample and the image acquisition device 16. If present in the optical path, the image improving element shown in FIG. 7, would change the direction of the optical path.

The depth of field (DOF) of optical detection assembly 15 may be such that the image acquisition area is well defined without significant interference from particles that are out of focus behind or in front of the image acquisition area.

When making optical sectioning the step size or the distance between to measurements in a sample may preferably be smaller than the DOF. This ensures that the particles are always imaged in focus.

In one embodiment of the invention the angle of the imaging system relative to the plane comprising the z-confinement is arranged to ensure that both the first and second confinement in the z-direction is within the image acquisition area of the sample. It is also preferred that the confinements in the y-direction are within the image acquisition area. This ensures that all particles in the part of the sample device under investigation may be detected and that any coding of the sample device is imaged. The coding of the confinement of the sample may be used for determination of the position of the sample device which again may be used for determination of the volume of the part of the sample measured.

In one embodiment of the invention none of the confinements in the z-direction or the y-direction are within the image acquisition area of the sample. In this case the volume of the sample in which the measurements has been carried out is determined using data regarding the optical magnification acquired in a calibration process previous to the measurement.

The skilled person will understand that having any combination of 0 or more of the z- and y-confinements within the image acquisition area may enable determination of the volume of the sample used for measurement, as long as data regarding the optical magnification has been determined for the confinements not within the image acquisition area before the measurement is started.

Figure 4:
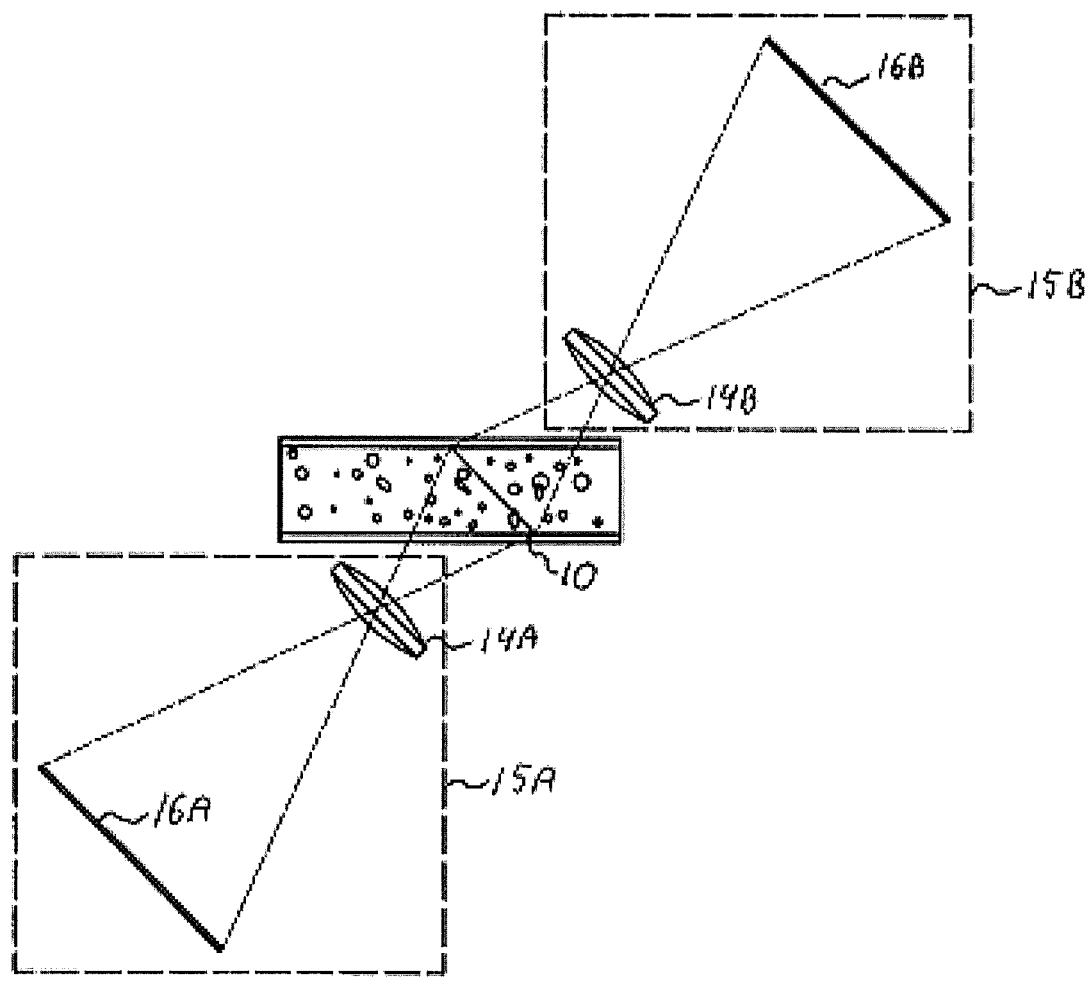
FIG. 4 shows a schematic side view of a measurement apparatus according to one embodiment of the invention to be used for 3D measurement of particles in a sample.

In FIG. 4 one embodiment of the invention comprising 2 optical detection assemblies are shown. A first optical assembly 15A comprising an image acquisition device 16A and an objective lens 14A is arranged to acquire images from one side of the sample device 18 while a second optical assembly 15B comprising an image acquisition device 16B and an objective lens 14B is arranged to acquire images from a substantially opposite direction. As shown for other embodiments, the sample may be translated and a series of images may be acquired. As the particles are imaged from substantially opposite directions, the information may be combined to get 3D information relating to the particles.

Figure 5:
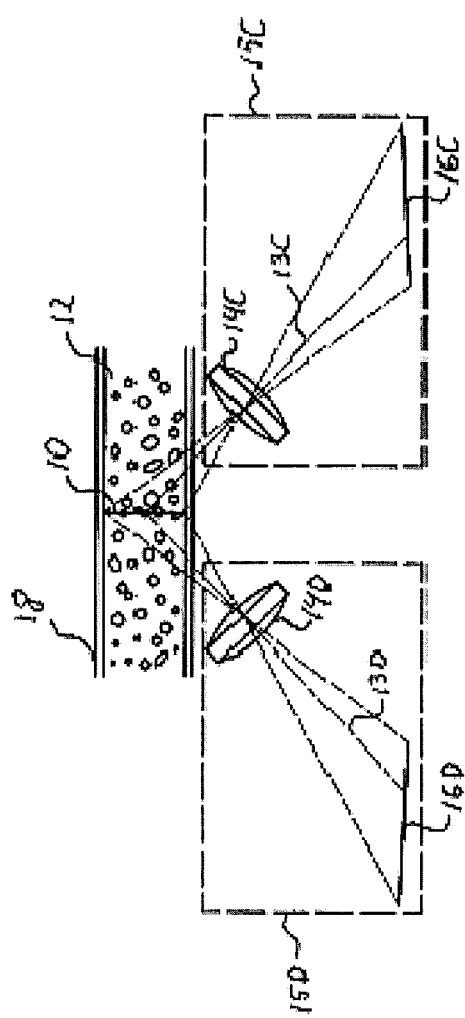
FIG. 5 shows a schematic side view of a measurement apparatus according one embodiment of the invention to be used for 3D measurement of particles in a sample.

In FIG. 5 one embodiment of the invention is shown. The setup comprises a first optical detection assembly 15C comprising an objective lens 14C and an image acquisition device 16C. The image acquisition device 16C are tilted relative to the optical axis 13 according to the Scheimpflug principle. The image acquisition area 10 is also tilted relative to the optical axis 10. The tilt is preferred to perpendicular to the confinements of the sample device 18 in order to make the image acquisition area cover the entire distance between the two confinements. The setup further may comprise a second optical detection assembly 15D comprising an objective lens 14D and an image acquisition device 16D. The image acquisition device 16d are tilted relative to the optical axis 13 according to the Scheimpflug principle. The image acquisition area 10 is also tilted relative to the optical axis 10. The tilt is preferred to perpendicular to the confinements of the sample device 18 in order to make the image acquisition area cover the entire distance between the two confinements. It is preferred that the two optical detection assemblies 15C and 15D share the image acquisition area 10 making 3D measurements of the particles in the sample 12 possible.

Figure 8:
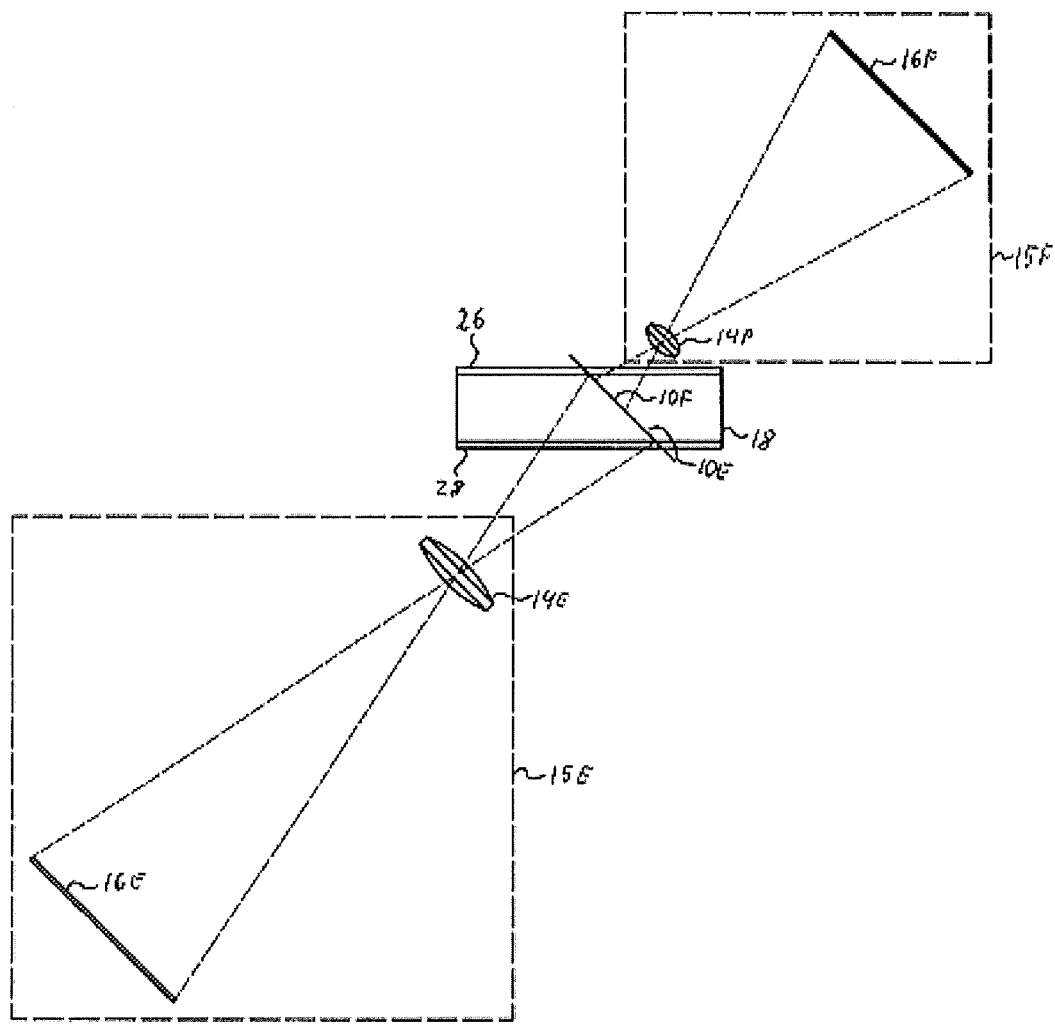
FIG. 8 shows a schematic side view of a measurement apparatus according to one embodiment of the invention wherein the optical magnification of the two lens systems is different.

In FIG. 8 one embodiment of the invention is shown. The setup comprises a first optical detection assembly 15E comprising an objective lens 14E and an image acquisition device 16E. The optical acquisition area 10E is arranged to comprise both the first confinement 26 and the second confinement 28. A second optical detection assembly 15F comprising an objective lens 15E and an image acquisition device 14F is arranged to have the optical acquisition area 10F coinciding with the image acquisition area 10E. The optical magnification of the second optical detection assembly 15F is larger than the optical magnification of the first optical detection assembly 15E. This setup is preferred to be used for scanning for particles using the first optical detection assembly 15E, and when found to investigate the particle under larger magnification using the second optical detection assembly 15F. The setup may also be used for acquiring 3D information about the particles found.

Figure 9:
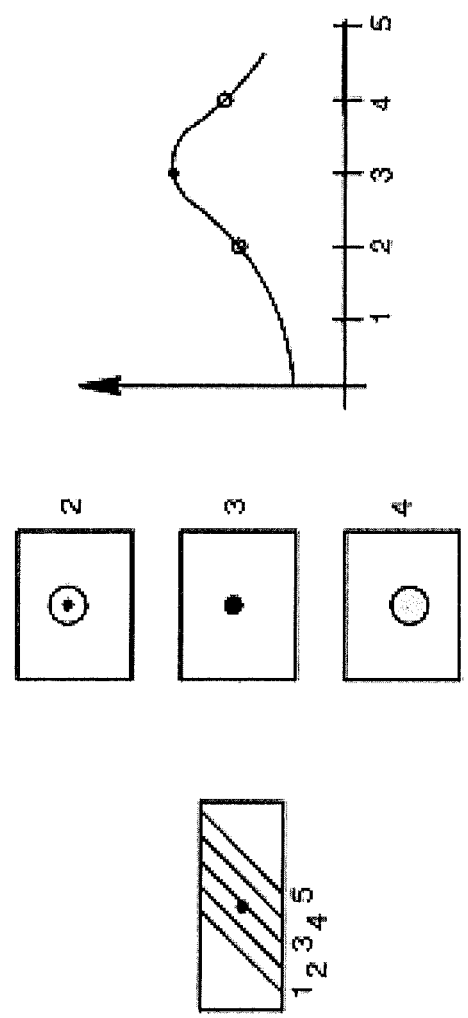
FIG. 9 shows a schematic view of the correlation between step size and the best focus of a particle.

In FIG. 9, a focus function is shown. The position of the images are given along the x-axis, while the y-axis may depict any given parameter which is suitable for determining whether a particle is in focus, such as contrast and brightness, and combinations of these.

Figure 10:
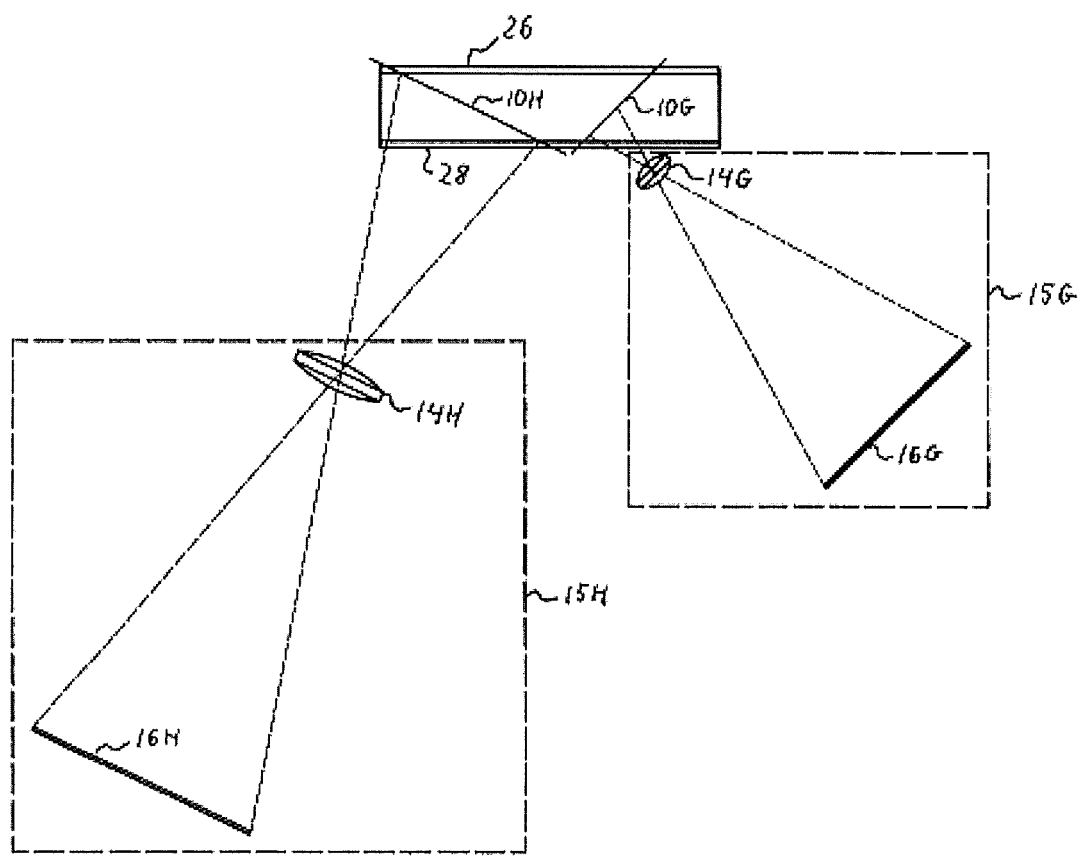
FIG. 10 shows a schematic side view of a measurement apparatus according to one embodiment of the invention wherein the optical magnification of the two lens systems are different.

In FIG. 10 one embodiment of the invention is shown. The Fig embodiment of the invention is embodiment is similar to the one shown in FIG. 8, except that the optical acquisition areas 10G and 10H is not coinciding. This setup is preferred to be used for samples moved in steps without pausing between single steps and image acquisitions. When a particle has been detected in image acquisition area 10H the same particle may be found in specific steps later in the image acquisition area 10G.

In FIG. 11B one embodiment of the invention is shown wherein an additional optical improving element 32 has been added to improve the quality of the acquired image. The optical improving element 32 is an iris, and the DOF of the optical detection assembly 15 depends of the size of the aperture created by the iris. Using a small aperture the DOF will be larger—see FIG. 11A and using a large aperture the DOF is made smaller—see FIG. 11B Any of the shown embodiments may be used for "Particle Tracking". In Particle Tracking a particle is observed as the particle is activated by e.g. ultra sonic waves or specific wavelengths of light (UV, IR), or as it changes during normal aging or changes due to chemical reaction or heat To get the best results of the observations, the particle should be at "stand-still", but if the sample is in liquid form, there may be small movements of the particles even though the particle is at "stand-still". E.g. the particles may settle during the observation period. The positions of the sample device relative to the camera may thus be adjusted dynamically during the observation period.

The observation may for example be done using a method comprising a number of individual or combined steps:

1. Position the sample device in the measurement setup
2. Activate the translation stage to move the sample device one step
3. Acquire an image of the sample in the sample device
4. Activate the image analyzing software to search the image for a particle of interest
5. If a particle has been found continue to next step, otherwise go back to step 2

In one embodiment, the observed particles are imaged in focus. Therefore the position of the sample device may need some fine adjustment to get the particle in best focus. The position of best focus may be determined by utilizing a focus function—see FIG. 9. If the particle is imaged at position 3, the image is in best focus, but if the particle is imaged at another position, e.g. position 2 or position 4, the activator should be activated to move the sample device to best focus. The observation procedure may therefore be continued using a method comprising the following individual or combined steps:

6. Activate the image analyzing software to determine the best focus plane for the particle.
7. If the particle is imaged in the best focus plane, then go to step 9
8. If the particle is imaged out of focus, then move the sample device to get the particle in best focus.
9. Start or continue the manipulation of the particle under investigation.
10. Acquire an image of the sample in then sample device.
11. Activate the image analyzing software to determine a change in the particle under investigation.
12. If investigation should continue, then go to step 6, else stop.

The images acquired and analyzed in step 10 may be stored for further analysis.

It should be emphasized that the embodiments described herein are in no way limiting and that many alternative embodiments are possible within the scope of the protection defined by the appended

The invention claimed is:

1. A method for obtaining a plurality of images of a liquid sample, the method comprising:
    a) arranging said liquid sample in relation to a sample device;
    b) arranging said sample device in relation to an apparatus having:
        at least a first optical detection assembly comprising at least a first image acquisition device, said first optical detection assembly having an optical axis and an object plane, said object plane comprising an image acquisition area from which electromagnetic waves can be detected as an image by said first image acquisition device;
        an image illumination device;
        at least one translation unit configured to move said sample device and said first optical detection assembly relative to each other; and
        said apparatus arranged to support said first optical detection assembly and said translation unit, wherein said first optical detection assembly and said translation unit are configured so that at least a part of said sample device is intersected by said image acquisition area;
    c) moving said sample device and said first detection assembly relative to each other over a scanning length, said movement comprising a movement in a direction along a first scanning path, which defines an angle theta relative to said optical axis, wherein theta is in the range of from about 0.3 to about 89.7 degrees, wherein said at least one translation unit moves said sample device and said at least one optical detection assembly relative to each other in a substantially continuous step-wise manner;
d) wherein electromagnetic waves are transmitted from the image illumination device through the image acquisition area towards the image acquisition device; and
e) obtaining said plurality of images, wherein the plurality of images are obtained with a predetermined time interval in between two successive images, wherein the predetermined time interval is in the range of from about $10^{-9}$ s to about $10^3$ s.

2. The method according to claim 1, further comprising analyzing said images recorded by said first image acquisition device, comprising identifying edges of objects in said images, wherein at least one pattern recognition algorithm is used to analyze said images for distinguishing between regions of different brightness in said images or for identifying transitions between brighter and darker regions in said image.

3. The method according to claim 2, wherein a number of images depicting adjacent parts of a given sample are analyzed to determine at which position of said object plane along said scanning path an object appearing in several of said images is in focus.

4. The method according to claim 3, comprising determining the area of said object in said images.

5. The method according to claim 4, wherein the position of said object plane along said scanning path at which said object is in focus is determined from a curve depicting the area of said object in said images versus the position along said scanning path.

6. The method according to claim 5, wherein at least one sample boundary of said sample to its surroundings is identified in at least one of said images.

7. The method according to claim 1, wherein when said sample is arranged in relation to the sample device comprising a support, said support is substantially parallel to said scanning path.

8. The method according to claim 7, wherein said sample is a drop of a liquid sample arranged on said support, said method comprising identifying a first sample boundary comprising an interface between said sample and said support, and identifying a second sample boundary comprising an interface between said sample and the surrounding atmosphere.

9. The method according to claim 8, comprising determining the separation of said first and second boundaries.

10. The method according to claim 9, comprising determining the analyzed volume of said sample from said separation of said first and second sample boundaries, the scanned length of said sample and the dimension of said image acquisition area.

11. The method according to claim 10, comprising determining the analyzed part of said volume of said sample from the separation of said first and second sample boundaries, the separation of a third and fourth sample boundaries, and the scanned length of said sample.

12. The method according to claim 1, further comprising reading information provided by a coding on said sample device, such as information relating to the position on the sample device, allowing a determination of the location along said scanning length where each of said plurality of images are acquired.

13. The method according to claim 1, comprising obtaining and analyzing images until a predetermined number of particles with a predetermined quality have been identified, and wherein the size of the imaged and analyzed part of said volume of said inhomogeneous liquid sample is determined.

14. The method according to claim 13, comprising determining the concentration of said particles with a predetermined quality in said inhomogeneous liquid sample from said predetermined number of particles with a predetermined quality and said size of the imaged and analyzed part of said volume.

15. The method according to claim 1, comprising obtaining said plurality of images by scanning said sample once along said scanning path.

16. The method according to claim 1, wherein said analysis combines a plurality of scans along said scanning path, each scan comprising at least one image.

17. The method according to claim 16, where at least one scan is made with a first step length and a first image resolution, where at least a second scan is made with a second step length and a second image resolution, and wherein said first step length is larger than or equal to said second step length, and wherein said first image resolution is lower than or equal to said second image resolution.

18. The method according to claim 1, comprising determining at least one parameter of a volume of an inhomogeneous liquid sample arranged in relation to said sample device.

19. The method according to claim 1, wherein said translation unit moves said sample device and said at least one optical detection assembly relative to each other in substantially identical steps of a predetermined step length in between two successive images, wherein the predetermined step length is in the range of from about 0.05 micrometers to 1000 micrometers.

20. The method according to claim 1, further comprising moving said sample device and said first optical detection assembly relative to each other along an axis having an angle to said scanning path.

21. The method according to claim 1, said first scanning path being selected from the group consisting of a scanning axis or a tangential to a rotational movement.

22. The method according to claim 1, where the sample is an inhomogeneous liquid sample.

23. A method for obtaining a plurality of images of an inhomogeneous liquid sample, said method comprising:
a) arranging said inhomogeneous liquid sample in relation to a sample device;
b) arranging said sample device in relation to an apparatus having:
at least a first optical detection assembly comprising at least a first image acquisition device, said first optical detection assembly having an optical axis and an object plane, said object plane comprising an image acquisition area from which electromagnetic waves can be detected as an image by said first image acquisition device;
an image illumination device;
at least one translation unit configured to move said sample device and said first optical detection assembly relative to each other; and
said apparatus arranged to support said first optical detection assembly and said translation unit, wherein said first optical detection assembly and said translation unit are configured so that at least a part of said sample device is intersected by said image acquisition area;
c) moving said sample device and said first detection assembly relative to each other over a scanning length, said movement comprising a movement in a direction along a first scanning path, which defines an angle theta relative to said optical axis, wherein theta is in the range of from about 0.3 to about 89.7 degrees, and wherein said at least one translation unit moves said sample device and said at least one optical detection assembly relative to each other in a substantially continuous stepwise manner;

d) wherein electromagnetic waves are transmitted from the image illumination device through the image acquisition area towards the image acquisition device; and e) obtaining said plurality of images, wherein the plurality of images are obtained with a predetermined time interval in between two successive images, wherein the predetermined time interval is in the range of from about $10^{-9}$ s to about $10^3$ s.

* * * * *